US012220549B2

(12) United States Patent
Na

(10) Patent No.: US 12,220,549 B2
(45) Date of Patent: *Feb. 11, 2025

(54) METHOD, SYSTEM, AND APPARATUS FOR DERMATOLOGICAL TREATMENT

(71) Applicant: Serendia, LLC, Lake Forest, CA (US)

(72) Inventor: Jongju Na, Songpa-Gu (KR)

(73) Assignee: Serendia, LLC, Lake Forest, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/680,754

(22) Filed: May 31, 2024

(65) Prior Publication Data
US 2024/0398663 A1   Dec. 5, 2024

Related U.S. Application Data

(63) Continuation of application No. 17/131,711, filed on Dec. 22, 2020, which is a continuation of application
(Continued)

(51) Int. Cl.
*A61H 39/08*   (2006.01)
*A61B 1/06*   (2006.01)
(Continued)

(52) U.S. Cl.
CPC ........... *A61M 37/00* (2013.01); *A61B 1/0655* (2022.02); *A61H 15/02* (2013.01); *A61H 39/002* (2013.01);
(Continued)

(58) Field of Classification Search
CPC .... A61H 15/02; A61H 39/086; A61H 39/002; A61H 39/007; A61H 23/02;
(Continued)

(56) References Cited

U.S. PATENT DOCUMENTS 6,277,116 B1   8/2001   Utely et al.
6,766,202 B2   7/2004   Underwood et al.
(Continued)

FOREIGN PATENT DOCUMENTS

KR   100719395 B1   5/2007
KR   100852500 B1   8/2008
(Continued)

OTHER PUBLICATIONS

IPR2024-00384, Patent Owner's Preliminary Response, (*Jeisys Medical Inc. and Ilooda Co., Ltd.* v. *Serendia, LLC*; U.S. Pat. No. 9,320,536), Apr. 24, 2024 (82 pages).
(Continued)

*Primary Examiner* — Tessa M Matthews
*Assistant Examiner* — David C Comstock
(74) *Attorney, Agent, or Firm* — Danielson Legal LLC

(57) ABSTRACT

Apparatus for treating dermatological tissue including a user holdable device having an end defining a surface configured to receive and capable of being releasably coupled to a needle module that includes a movable needle assembly having a plurality of needles that is located past the end of the device when the module is releasably coupled to the device. The device includes a motor capable of moving the assembly to deploy the needles to penetrate dermatological tissue to a selectable desired depth. The apparatus includes a signal generator capable of being coupled to the needles to provide a radio frequency signal having a selectable intensity; at least one processor configured to provide a signal to cause the motor to deploy the needles to the desired depth and a signal to cause the signal generator to provide the intensity of the radio frequency signal to the needles; and at least one display.

18 Claims, 21 Drawing Sheets

Related U.S. Application Data

No. 15/724,261, filed on Oct. 3, 2017, now Pat. No. 10,869,812, which is a continuation of application No. 15/096,686, filed on Apr. 12, 2016, now Pat. No. 9,775,774, which is a continuation of application No. 13/825,083, filed as application No. PCT/KR2012/001335 on Feb. 22, 2012, now Pat. No. 9,320,536, which is a continuation of application No. 13/060,274, filed on Mar. 30, 2011, now Pat. No. 8,979,912.

(60) Provisional application No. 61/449,080, filed on Mar. 3, 2011.

(51) Int. Cl.

| | | |
|---|---|---|
| *A61H 15/02* | (2006.01) | |
| *A61H 39/00* | (2006.01) | |
| *A61M 37/00* | (2006.01) | |
| *A61N 1/05* | (2006.01) | |
| *A61N 1/30* | (2006.01) | |
| *A61N 1/32* | (2006.01) | |
| *A61N 1/36* | (2006.01) | |
| *A61N 5/06* | (2006.01) | |
| A61B 17/34 | (2006.01) | |
| A61H 15/00 | (2006.01) | |
| A61H 23/02 | (2006.01) | |

(52) U.S. Cl.
CPC ......... *A61H 39/007* (2013.01); *A61H 39/086* (2013.01); *A61N 1/0502* (2013.01); *A61N 1/30* (2013.01); *A61N 1/328* (2013.01); *A61N 1/36017* (2013.01); *A61N 5/0616* (2013.01); *A61N 5/062* (2013.01); *A61N 5/0624* (2013.01); *A61B 2017/3409* (2013.01); *A61H 2015/0014* (2013.01); *A61H 23/02* (2013.01); *A61H 2039/005* (2013.01); *A61H 2201/0153* (2013.01); *A61H 2201/105* (2013.01); *A61H 2201/1207* (2013.01); *A61H 2201/1604* (2013.01); *A61H 2201/169* (2013.01); *A61H 2201/5007* (2013.01); *A61H 2201/5097* (2013.01); *A61H 2205/022* (2013.01); *A61H 2205/04* (2013.01); *A61H 2205/06* (2013.01); *A61H 2205/065* (2013.01); *A61H 2205/084* (2013.01); *A61H 2205/10* (2013.01); *A61H 2205/12* (2013.01); *A61M 2037/0007* (2013.01); *A61M 37/0015* (2013.01); *A61M 2037/0023* (2013.01); *A61M 2037/0046* (2013.01); *A61M 2037/0061* (2013.01); *A61M 2205/8206* (2013.01); *A61N 2005/0644* (2013.01); *A61N 2005/0652* (2013.01); *A61N 2005/0659* (2013.01); *A61N 2005/0661* (2013.01)

(58) Field of Classification Search
CPC ...... A61H 2015/0014; A61H 2039/005; A61H 2201/105; A61H 2201/1207; A61H 2201/1604; A61H 2201/169; A61H 2201/5007; A61H 2201/5097; A61M 37/00; A61M 2037/0007; A61M 2037/0023; A61M 2205/8206; A61N 1/0502; A61N 1/328; A61N 1/36017; A61N 5/0616; A61N 5/062; A61N 5/0624; A61N 2005/0644; A61N 2005/0652; A61N 2005/0659; A61N 2005/0661; A61B 2017/3409

USPC ....... 606/9, 186; 600/249; 607/88, 102, 115, 607/189; 604/20, 21, 46, 117; 601/2; 424/1.11
See application file for complete search history.

(56) References Cited

U.S. PATENT DOCUMENTS

| | | | |
|---|---|---|---|
| 6,770,071 | B2 | 8/2004 | Woloszko et al. |
| 6,890,319 | B1 | 5/2005 | Crocker |
| 7,618,429 | B2 * | 11/2009 | Mulholland ......... A61B 17/205 |
| | | | 606/186 |
| 7,824,394 | B2 | 11/2010 | Manstein |
| 8,012,153 | B2 | 9/2011 | Woloszko et al. |
| 8,142,426 | B2 | 3/2012 | Knopp et al. |
| 8,540,705 | B2 | 9/2013 | Mehta |
| 8,608,737 | B2 | 12/2013 | Mehta et al. |
| 8,900,231 | B2 | 12/2014 | Kreindel |
| 9,095,358 | B2 | 8/2015 | Woloszko et al. |
| 9,510,899 | B2 | 12/2016 | Manstein |
| 10,799,285 | B2 | 10/2020 | Mulholland |
| 10,869,812 | B2 | 12/2020 | Na |
| 2002/0120260 | A1 | 8/2002 | Morris et al. |
| 2002/0120261 | A1 | 8/2002 | Morris et al. |
| 2003/0130711 | A1 | 7/2003 | Pearson et al. |
| 2004/0058882 | A1 | 3/2004 | Eriksson et al. |
| 2006/0036210 | A1 | 2/2006 | Zhang et al. |
| 2007/0208340 | A1 | 9/2007 | Ganz et al. |
| 2008/0082090 | A1 | 4/2008 | Manstein |
| 2008/0091135 | A1 * | 4/2008 | Draghia-Akli ......... A61N 1/327 |
| | | | 604/20 |
| 2008/0091182 | A1 | 4/2008 | Mehta |
| 2009/0048557 | A1 * | 2/2009 | Yeshurun ............. A61B 18/203 |
| | | | 604/20 |
| 2011/0288543 | A1 | 11/2011 | Cheng et al. |

FOREIGN PATENT DOCUMENTS

| | | |
|---|---|---|
| KR | 200441552 Y1 | 8/2008 |
| WO | WO2007064718 A2 | 6/2007 |
| WO | WO2008005477 A2 | 1/2008 |
| WO | WO2010016848 A1 | 2/2010 |

OTHER PUBLICATIONS

IPR2024-00384, Patent Owner Serendia Llc's Motion to Seal, (*Jeisys Medical Inc. and Ilooda Co., Ltd.* v. *Serendia, LLC*; U.S. Pat. No. 9,320,536), Apr. 24, 2024 (10 pages).
IPR2024-00384, *Jeisys* v. *Serendia*; Complainant's Jul. 24, 2023 Supplemental Validity Contentions, Case 337-TA-1356, Exhibit 2003, (425 pages).
IPR2024-00384, *Jeisys* v. *Serendia*; Expert Report of Jean Woloszko, Case 337-TA-1356, Exhibit 2004, (684 pages).
IPR2024-00384, *Jeisys* v. *Serendia*; Deposition transcript of Jean Woloszko taken Sep. 14, 2023, Case 337-TA-1356, Exhibit 2007, (2 pages).
IPR2024-00384, *Jeisys* v. *Serendia*; Deposition transcript of Jean Woloszko taken Sep. 15, 2023, Case 337-TA-1356, Exhibit 2008, (2 pages).
IPR2024-00384, *Jeisys* v. *Serendia*; Complainant's Public Interest Statement & Complaint of Serendia, Case 337-TA-_, Exhibit 2016, (74 pages).
IPR2024-00384, *Jeisys* v. *Serendia*; The Parties' Proposed Procedural Schedule and Notice of Proceedings and state and federal litigation pursuant to order No. 3, Case 337-TA-1356, Exhibit 2017, (26 pages).
IPR2024-00384, *Jeisys* v. *Serendia*; Order No. 6 Adopted Procedural Schedule dated Apr. 27, 2023, Case 337-TA-1356, Exhibit 2018, (12 pages).
IPR2024-00384, *Jeisys* v. *Serendia*; Respondents' Joint Reply Post-Hearing Brief, Case 337-TA-1356, Exhibit 2019, (6 pages).
IPR2024-00384, *Jeisys* v. *Serendia*; Response of Ilooda to the Complaint and Notice of Investigation, Case 337-TA-1356, Exhibit 2020, (88 pages).

(56) References Cited

OTHER PUBLICATIONS

IPR2024-00384, *Jeisys v. Serendia;* Jeisys and Cynosure's Response to the Complaint and Notice of Investigation, Case 337-TA-1356, Exhibit 2021, (68 pages).
IPR2024-00384, *Jeisys v. Serendia;* Letter from Merle W. Richman to Cutera dated Mar. 20, 2018, Exhibit 2022, (1 page).
IPR2024-00384, *Jeisys v. Serendia;* Letter from Keith K. Im to Cynosure dated Nov. 29, 2021, Exhibit 2023, (2 pages).
IPR2024-00384, *Jeisys v. Serendia;* Order No. 33 Granting Parties' Joint Motion to Amend the Amended Procedural Schedule dated Oct. 19, 2023, Case 337-TA-1356, Exhibit 2024, (5 pages).
IPR2024-00384, *Jeisys v. Serendia;* Brochure Sylfirm X Dual Wave RF Microneedling System, Exhibit 2037, (16 pages).
IPR2024-00384, *Jeisys v. Serendia;* Respondents' Notice of Prior Art, Case 337-TA-1356, Exhibit 2053, (11 pages).
IPR2024-00384, *Jeisys v. Serendia;* Sylfirm X Revolutionizes Clinical Applications of RF Microneedling dated May/Jun. 2022, Exhibit 2066, (3 pages).
IPR2024-00384, *Jeisys v. Serendia;* World-Class Product of Korea 2020 Certificate to ViOL dated Dec. 9, 2020, Exhibit 2067, (1 page).
IPR2024-00384, *Jeisys v. Serendia;* Vincent A. Thomas CV, Exhibit 2070, (17 pages).
IPR2024-00384, *Jeisys v. Serendia;* ViOL, Sylfirm X User Manual, Exhibit 2083, (43 pages).
IPR2024-00384, *Jeisys v. Serendia;* Sylfirm X Product Photographs, Exhibit 2086, (11 pages).
IPR2024-00384, *Jeisys v. Serendia;* Sylfirm X Introduction Video 1.mp4, "New X Tips", Exhibit 2097.
IPR2024-00384, *Jeisys v. Serendia;* Transcript of Sylfirm X Introduction Video 1 "Sylfirm X. New X Tips", Exhibit 2098, (1 page).
IPR2024-00384, *Jeisys v. Serendia;* Deposition Transcript of Peter Crosby taken Sep. 4, 2023, Case 337-TA-1356, Exhibit 2103, (2 pages).
IPR2024-00384, *Jeisys v. Serendia;* Deposition Transcript of Peter Crosby taken Sep. 5, 2023, Case 337-TA-1356, Exhibit 2104, (2 pages).
IPR2024-00384, *Jeisys v. Serendia;* U.S. Patent Application Publication No. 20020120260 A1, Exhibit 2108, (67 pages).
IPR2024-00384, *Jeisys v. Serendia;* Certified English translation of Korean Registered Patent Publication No. KR10-0852500, Exhibit 2110, (11 pages).
IPR2024-00384, *Jeisys v. Serendia;* Respondents' Amended Notice of Prior Art, Case 337-TA-1356, Exhibit 2111, (11 pages).
IPR2024-00384, *Jeisys v. Serendia;* U.S. Pat. No. 6,890,319 B1, Exhibit 2115, (18 pages).
IPR2024-00384, *Jeisys v. Serendia;* U.S. Pat. No. 10,869,812 B2, Exhibit 2116, (32 pages).
IPR2024-00384, *Jeisys v. Serendia;* U.S. Pat. No. 8,540,705 B2, Exhibit 2117, (51 pages).
IPR2024-00384, *Jeisys v. Serendia;* USPTO File History for U.S. Pat. No. 10,869,812, Exhibit 2118, (733 pages).
IPR2024-00384, *Jeisys v. Serendia;* U.S. Pat. No. 6,277,116 B1, Exhibit 2119, (22 pages).
IPR2024-00384, *Jeisys v. Serendia;* U.S. Patent Application Publication No. 20020120261 A1, Exhibit 2120, (62 pages).
IPR2024-00384, *Jeisys v. Serendia;* Cartessa Aesthetics, Innovation in RF Microneedling: A closer look at VirtueRF, Jun. 2021, Exhibit 2122, (4 pages).
IPR2024-00384, *Jeisys v. Serendia;* Woloszko Hearing Transcript dated Nov. 7, 2023, Case 337-TA-1356, Exhibit 2125, (69 pages).
IPR2024-00384, *Jeisys v. Serendia;* Crosby Hearing Transcript dated Dec. 12, 2023, Case 337-TA-1356, Exhibit 2126, (31 pages).
IPR2024-00384, *Jeisys v. Serendia;* Crosby Opening Expert Report - Appendix 17, Exhibit 2127, (11 pages).
IPR2024-00384, *Jeisys v. Serendia;* Deposition transcript of Jongju Na dated Jul. 25, 2023, Case 337-TA-1356, Exhibit 2128, (5 pages).
IPR2024-00384, *Jeisys v. Serendia;* Sylfirm X Product Photographs, Exhibit 2130, (4 pages).
IPR2024-00384, *Jeisys v. Serendia;* U.S. Patent Application Publication No. 20060036210A1, Exhibit 2132, (69 pages).
IPR2024-00384, Declaration of Peter Crosby in Support Of Patent Owner's Preliminary Response, (*Jeisys Medical Inc. and Ilooda Co., Ltd.* v. *Serendia, LLC;* U.S. Pat. No. 9,320,536), Exhibit 2134 (65 pages).
IPR2024-00384, Declaration of Vince Thomas in Support of Patent Owner's Preliminary Response, (*Jeisys Medical Inc. and Ilooda Co., Ltd.* v. *Serendia, LLC;* U.S. Pat. No. 9,320,536), Exhibit 2135 (8 pages).
IPR2024-00384, *Jeisys v. Serendia;* Peter Crosby CV, Exhibit 2136, (8 pages).
IPR2024-00384, *Jeisys v. Serendia;* Appendix 5—Summary Invalidity Claim Chart; U.S. Pat. No. 9,320,536, Case 337-TA-1356, Exhibit 2137, (5 pages).
IPR2024-00384, *Jeisys v. Serendia;* USPTO Statutory Disclaimer dated Apr. 19, 2024, U.S. Appl. No. 13/825,083, Exhibit 2138, (11 pages).
510k Summary—K082391; Primaeva Medical Inc., RX-0486, 2009, 5 Pages.
Berube et al., "A Predictive Model of Minimally Invasive Bipolar Fractional Radiofrequency Skin Treatment", Lasers in Surgery and Medicine 41:473-478 (2009), RX-1567, 6 Pages.
Berube et al., "A Predictive Model of Minimally Invasive Bipolar Fractional Radiofrequency Skin Treatment", Lasers in Surgery and Medicine 41:473-478 (2009), CX-0752, 6 Pages.
Alexiades-Armenakas et al., "Blinded, Randomized, Quantitative Grading Comparison of Minimally Invasive, Fractional Radiofrequency and Surgical Face-lift to Treat Skin Laxity", Arch Dermatol. 2010; vol. 146(4):396-405, 10 Pages.
D & PS, Magazine for Dermatologists & Plastic Surgeons, Nexgen®, 2010, CX-2622, 13 Pages.
Primaeva Medical Instructions, Primaeva Medical Inc., Miratone™ System, Exhibit# Berube 9, Jul. 26, 2023, 27 Pages.
Primaeva Medical User Manual, Exhibit# Berube 10, CX-0946, Jul. 26, 2023, 39 Pages.
Scarlett Website, CX-2612, Jan. 10, 2011, 16 Pages.
Shim DKU Thesis, "How Fractional micro-needle RF Works and How it Affects Skin Tissue", Department of Medical Laser, 2010, 57 Pages.
Evidentiary Hearing with excerpts dated Dec. 11, 2023; vol. 5, Case 337-TA-1356, 161 Pages.
Evidentiary Hearing with excerpts dated Dec. 12, 2023; vol. 6, Case 337-TA-1356, 144 Pages.
Evidentiary Hearing with excerpts dated Nov. 1, 2023; vol. 1, Case 337-TA-1356, 144 Pages.
Evidentiary Hearing with excerpts dated Nov. 2, 2023; vol. 2, Case 337-TA-1356, 114 Pages.
Evidentiary Hearing with excerpts dated Nov. 6, 2023; vol. 3, Case 337-TA-1356, 76 Pages.
Evidentiary Hearing with excerpts dated Nov. 7, 2023; vol. 4, Case 337-TA-1356, 271 Pages.
IPR2024-00386, *Jeisys v. Serendia;* U.S. Pat. No. 8,142,426 B2 (Knopp), Exhibit 2058, (35 pages).
IPR2024-00386, *Jeisys v. Serendia;* Berube et al., A Predictive Model, Laser in Surgery and Medicine; Exhibit 2060, (6 pages).
IPR2024-00386, *Jeisys v. Serendia;* Sylfirm Video2.mov, "Victory of Life, ViOL"; Exhibit 2063.
IPR2024-00386, *Jeisys v. Serendia;* Transcript of Sylfirm Video2; Exhibit 2064, (1 page).
IPR2024-00386, *Jeisys v. Serendia;* Braun, Sylfirm X article; Exhibit 2066, (3 pages).
IPR2024-00386, *Jeisys v. Serendia;* World-Class Product of Korea 2020 Certificate to ViOL (Dec. 9, 2020); Exhibit 2067, (1 page).
IPR2024-00386, *Jeisys v. Serendia;* Allure article, A New Filler for Laugh Lines & More Procedures That Are Safe for Dark Skin; Exhibit 2069, (10 pages).
IPR2024-00386, *Jeisys v. Serendia;* Vincent A. Thomas CV; Exhibit 2070, (17 pages).
IPR2024-00386, *Jeisys v. Serendia;* Daniel W. van de Weide CV; Exhibit 2072, (43 pages).
IPR2024-00386, *Jeisys v. Serendia;* C.L. Brace, Microwave ablation with a Triaxial Antenna Results in Ex Vivo Bovine Liver, vol. 53, No. 1, Jan. 2005; Exhibit 2073, (6 pages).

(56) References Cited

OTHER PUBLICATIONS

IPR2024-00386, *Jeisys v. Serendia;* D. Haemmerich, Finite-Element Analysis of Hepatic Multiple Probe Radio-Frequency Ablation, vol. 49, No. 7, Jul. 2002; Exhibit 2074, (7 pages).

IPR2024-00386, *Jeisys v. Serendia;* L. Zilberti, Charge Relaxation in Biological Tissues with Extremely High Permittivity, published on May 24, 2016; Exhibit 2075, (7 pages).

IPR2024-00386, *Jeisys v. Serendia;* pt. 1 IEC Int'l Standard, Medical Electrical Equipment—Part 2-2 (6.0 ed); Exhibit 2076, (190 pages).

IPR2024-00386, *Jeisys v. Serendia;* IEC Int'l Standard, Medical Electrical Equipment—Part 2-2 (5.0 ed—Withdrawn); Exhibit 2077, (166 pages).

IPR2024-00386, *Jeisys v. Serendia;* Abstract—IEC Int'l Standard, Medical Electrical Equipment—Part 2-2 (5.0 ed—Withdrawn); Exhibit 2078, (1 page).

IPR2024-00386, *Jeisys v. Serendia;* Sylfirm X (product information); Exhibit 2079, (5 pages).

IPR2024-00386, *Jeisys v. Serendia;* ViOL, Sylfirm X User Manual; Exhibit 2083, (43 pages).

IPR2024-00386, *Jeisys v. Serendia;* Sylfirm X Product Photographs; Exhibit 2086, (11 pages).

IPR2024-00386, *Jeisys v. Serendia;* D. van der Weide, Presentation-RF Microneedle Arrays: Thermal Results; Exhibit 2087, (12 pages).

IPR2024-00386, *Jeisys v. Serendia;* Photographs—Accused Product Examinations (Jun.-Aug. 2023); Exhibit 2088, (44 pages).

IPR2024-00386, *Jeisys v. Serendia;* Product photo (CX-3378C.1); Exhibit 2091, (1 page).

IPR2024-00386, *Jeisys v. Serendia;* Product photo (CX-3379C.1); Exhibit 2092, (1 page).

IPR2024-00386, *Jeisys v. Serendia;* Product photo (CX-3380C.1); Exhibit 2093, (1 page).

IPR2024-00386, *Jeisys v. Serendia;* Product photo (CX-3381C.1); Exhibit 2094, (1 page).

IPR2024-00386, *Jeisys v. Serendia;* Shin & Kim, Radiofrequency in Clinical Dermatology, accepted on Nov. 8, 2013; Exhibit 2095 (9 pages).

IPR2024-00386, *Jeisys v. Serendia;* Ahn & Cho, Invasive Pulse-Type, Bipolar, Alternating Current Radiofrequency Treatment using Microneedle Electrodes for Nasal Rosacea, accepted on Jun. 12, 2017; Exhibit 2096, (5 pages).

IPR2024-00386, *Jeisys v. Serendia;* Sylfirm X Introduction Video 1.mp4, "New X Tips"; Exhibit 2097.

IPR2024-00386, *Jeisys v. Serendia;* Transcript of Sylfirm X Introduction Video 1; Exhibit 2098, (1 page).

IPR2024-00386, *Jeisys v. Serendia;* Sylfirm X Introduction Video 2.mov, "Victory of Life, ViOL"; Exhibit 2099.

IPR2024-00386, *Jeisys v. Serendia;* Transcript of Sylfirm X Introduction Video 2; Exhibit 2100, (1 page).

IPR2024-00386, *Jeisys v. Serendia;* Press Release-BENEV Launches Sylfirm X Ultimate Edition (Apr. 26, 2021); Exhibit 2101, (4 pages).

IPR2024-00386, Declaration of Vincent A. Thomas in Support of Patent Owner's Preliminary Response (*Ilooda Co., Ltd and Jeisys Medical Inc. v. Serendia, LLC;* U.S. Pat. No. 9,480,836), (8 pages).

IPR2024-00383, Patent Owner's Preliminary Response (*Jeisys Medical Inc. and Ilooda Co., Ltd. v. Serendia, LLC;* U.S. Pat. No. 9,775,774), Apr. 23, 2024 (81 pages).

IPR2024-00383, Patent Owner Motion to Seal (*Jeisys Medical Inc. and Ilooda Co., Ltd. v. Serendia, LLC;* U.S. Pat. No. 9,775,774), Apr. 23, 2024 (10 pages).

IPR2024-00383, *Jeisys v. Serendia;* Complainant's Jul. 24, 2023 Supplemental Validity Contentions, Case 337-TA-1356, Exhibit 2003, (425 pages).

IPR2024-00383, *Jeisys v. Serendia;* Expert Report of Jean Woloszko, Case 337-TA-1356, Exhibit 2004, (684 pages).

IPR2024-00383, *Jeisys v. Serendia;* Deposition transcript of Jean Woloszko taken Sep. 14, 2023, Case 337-TA-1356, Exhibit 2007, (2 pages).

IPR2024-00383, *Jeisys v. Serendia;* Deposition transcript of Jean Woloszko taken Sep. 15, 2023, Case 337-TA-1356, Exhibit 2008, (2 pages).

IPR2024-00383, *Jeisys v. Serendia;* Complainant's Public Interest Statement & Complaint of Serendia, Case 337-TA-_, Exhibit 2016, (74 pages).

IPR2024-00383, *Jeisys v. Serendia;* The Parties' Proposed Procedural Schedule and Notice of Proceedings and State and Federal Litigation Pursuant to Order No. 3, Case 337-TA-1356, Exhibit 2017, (26 pages).

IPR2024-00383, *Jeisys v. Serendia;* Order No. 6 Adopted Procedural Schedule, Case 337-TA-1356, Exhibit 2018, (12 pages).

IPR2024-00383, *Jeisys v. Serendia;* Respondents' Joint Reply Post-Hearing Brief, Case 337-TA-1356, Exhibit 2019, (6 pages).

IPR2024-00383, *Jeisys v. Serendia;* Response of Ilooda to the Complaint and Notice of Investigation, Case 337-TA-1356, Exhibit 2020, (88 pages).

IPR2024-00383, *Jeisys v. Serendia;* Jeisys and Cynosure's Response to the Complaint and Notice of Investigation, Case 337-TA-1356, Exhibit 2021, (68 pages).

IPR2024-00383, *Jeisys v. Serendia;* Letter from Merle W. Richman to Cutera dated Mar. 20, 2018, Exhibit 2022, (1 page).

IPR2024-00383, *Jeisys v. Serendia;* Letter from Keith K. Im to Cynosure dated Nov. 29, 2021, Exhibit 2023, (2 pages).

IPR2024-00383, *Jeisys v. Serendia;* Order No. 33 Granting Parties' Joint Motion to Amend the Amended Procedural Schedule dated Oct. 19, 2023, Case 337-TA-1356, Exhibit 2024, (5 pages).

IPR2024-00383, *Jeisys v. Serendia;* Brochure Sylfirm X Dual Wave RF Microneedling System, Exhibit 2037, (16 pages).

IPR2024-00383, *Jeisys v. Serendia;* Respondents' Notice of Prior Art; Case 337-TA-1356, Exhibit 2053, (11 page).

IPR2024-00383, *Jeisys v. Serendia;* Sylfirm X Revolutionizes Clinical Applications of RF Microneedling dated May/ Jun. 2022, Exhibit 2066, (3 pages).

IPR2024-00383, *Jeisys v. Serendia;* World-Class Product of Korea 2020 Certificate to ViOL (Dec. 9, 2020); Exhibit 2067, (1 page).

IPR2024-00383, *Jeisys v. Serendia;* Vincent A. Thomas CV; Exhibit 2070, (17 pages).

IPR2024-00383, *Jeisys v. Serendia;* ViOL, Sylfirm X User Manual; Exhibit 2083, (43 pages).

IPR2024-00383, *Jeisys v. Serendia;* Sylfirm X Product Photographs; Exhibit 2086, (11 pages).

IPR2024-00383, *Jeisys v. Serendia;* Sylfirm X Introduction Video 1.mp4, "New X Tips"; Exhibit 2097.

IPR2024-00383, *Jeisys v. Serendia;* Transcript of Sylfirm X Introduction Video 1; Exhibit 2098, (1 page).

IPR2024-00383, *Jeisys v. Serendia;* Deposition Transcript of Peter Crosby taken Sep. 4, 2023, Case 337-TA-1356, Exhibit 2103, (2 pages).

IPR2024-00383, *Jeisys v. Serendia;* Deposition Transcript of Peter Crosby taken Sep. 5, 2023, Case 337-TA-1356, Exhibit 2104, (2 pages).

IPR2024-00383, *Jeisys v. Serendia;* USPTO Statutory Disclaimer dated Apr. 19, 2024, U.S. Appl. No. 15/096,686, Exhibit 2105, (11 pages).

IPR2024-00383, *Jeisys v. Serendia;* U.S. Patent Application Publication No. 20020120260 A1, Exhibit 2108, (67 pages).

IPR2024-00383, *Jeisys v. Serendia;* U.S. Patent Application Publication No. 20030130711 A1, Exhibit 2109, (54 pages).

IPR2024-00383, *Jeisys v. Serendia;* Certified English translation of Korean Registered Patent Publication No. KR10-0852500, Exhibit 2110, (11 pages).

IPR2024-00383, *Jeisys v. Serendia;* Respondents' Amended Notice of Prior Art, Case 337-TA-1356, Exhibit 2111, (11 pages).

IPR2024-00383, *Jeisys v. Serendia;* Appendix 6—Summary Invalidity Claim Chart; U.S. Pat. No. 9,775,774, Case 337-TA-1356, Exhibit 2113, (1 page).

IPR2024-00383, *Jeisys v. Serendia;* USPTO File History for U.S. Pat. No. 9,320,536, Exhibit 2114, (362 pages).

IPR2024-00383, *Jeisys v. Serendia;* U.S. Pat. No. 6,890,319 B1, Exhibit 2115, (18 pages).

IPR2024-00383, *Jeisys v. Serendia;* U.S. Pat. No. 10,869,812 B2, Exhibit 2116, (32 pages).

(56) References Cited

OTHER PUBLICATIONS

IPR2024-00383, *Jeisys* v. *Serendia;* U.S. Pat. No. 8,540,705 B2, Exhibit 2117, (51 pages).
IPR2024-00383, *Jeisys* v. *Serendia;* USPTO File History for U.S. Pat. No. 10,869,812, Exhibit 2118, (733 pages).
IPR2024-00383, *Jeisys* v. *Serendia;* U.S. Pat. No. 6,277,116 B1, Exhibit 2119, (22 pages).
IPR2024-00383, *Jeisys* v. *Serendia;* U.S. Patent Application Publication No. 20020120261 A1, Exhibit 2120, (62 pages).
IPR2024-00383, *Jeisys* v. *Serendia;* Cartessa Aesthetics, Innovation in RF Microneedling: A closer look at VirtueRF, Jun. 2021, Exhibit 2122, (4 pages).
IPR2024-00383, Declaration of Peter Crosby in Support of Patent Owner's Preliminary Response, (*Jeisys Medical Inc. and Ilooda Co., Ltd.* v. *Serendia, LLC;* U.S. Pat. No. 9,775,774), Exhibit 2123 (63 pages).
IPR2024-00383, Declaration of Vince Thomas in Support of Patent Owner's Preliminary Response, (*Jeisys Medical Inc. and Ilooda Co., Ltd.* v. *Serendia, LLC;* U.S. Pat. No. 9,775,774), Exhibit 2124 (8 pages).
IPR2024-00383, *Jeisys* v. *Serendia;* Woloszko Hearing Transcript dated Nov. 7, 2023, Case 337-TA-1356, Exhibit 2125, (69 pages).
IPR2024-00383, *Jeisys* v. *Serendia;* Crosby Hearing Transcript dated Dec. 12, 2023, Case 337-TA-1356, Exhibit 2126, (31 pages).
IPR2024-00383, *Jeisys* v. *Serendia;* Crosby Opening Expert Report—Appendix 17, Exhibit 2127, (11 pages).
IPR2024-00383, *Jeisys* v. *Serendia;* Deposition transcript of Jongju Na dated Jul. 25, 2023, Case 337-TA-1356, Exhibit 2128, (5 pages).
IPR2024-00383, *Jeisys* v. *Serendia;* Sylfirm X Product Photographs, Exhibit 2130, (4 pages).
IPR2024-00383, *Jeisys* v. *Serendia;* Peter Crosby CV, Exhibit 2136, (8 pages).
IPR2024-00386, Patent Owner's Preliminary Response (*Ilooda Co., Ltd and Jeisys Medical Inc.* v. *Serendia, LLC;* U.S. Pat. No. 9,480,836), Apr. 25, 2024 (87 pages).
IPR2024-00386, Patent Owner Motion to Seal (*Ilooda Co., Ltd and Jeisys Medical Inc.* v. *Serendia, LLC;* U.S. Pat. No. 9,480,836), Apr. 25, 2024 (10 pages).
IPR2024-00386, *Jeisys* v. *Serendia;* Complainant's Jul. 24, 2023 Supplemental Validity Contentions, Case 337-TA-1356, Exhibit 2003, (425 pages).
IPR2024-00386, *Jeisys* v. *Serendia;* Expert Report of Jean Woloszko, Case 337-TA-1356, Exhibit 2004, (684 pages).
IPR2024-00386, *Jeisys* v. *Serendia;* Deposition transcript of Jean Woloszko taken Sep. 14, 2023, Case 337-TA-1356, Exhibit 2007, (2 pages).
IPR2024-00386, *Jeisys* v. *Serendia;* Deposition transcript of Jean Woloszko taken Sep. 15, 2023, Case 337-TA-1356, Exhibit 2008, (2 pages).
IPR2024-00386, *Jeisys* v. *Serendia;* Deposition transcript of Daniel W. van der Weide taken Aug. 31, 2023, Case 337-TA-1356, Exhibit 2009, (2 pages).
IPR2024-00386, *Jeisys* v. *Serendia;* Deposition transcript of Daniel W. van der Weide taken Sep. 1, 2023, Case 337-TA-1356, Exhibit 2010, (2 pages).
IPR2024-00386, *Jeisys* v. *Serendia;* Deposition transcript of David J. Goldberg taken Sep. 15, 2023, Case 337-TA-1356, Exhibit 2011, (2 pages).
IPR2024-00386, *Jeisys* v. *Serendia;* Hearing transcript held Nov. 7, 2023, Case 337-TA-1356, Exhibit 2012, (18 pages).
IPR2024-00386, *Jeisys* v. *Serendia;* Hearing transcript held Dec. 12, 2023, Case 337-TA-1356, Exhibit 2013, (9 pages).
IPR2024-00386, *Jeisys* v. *Serendia;* Hearing transcript held Dec. 11, 2023, Case 337-TA-1356, Exhibit 2014, (14 pages).
IPR2024-00386, *Jeisys* v. *Serendia;* Complainant's Public Interest Statement & Complaint of Serendia, Case 337-TA-_, Exhibit 2016, (74 pages).

IPR2024-00386, *Jeisys* v. *Serendia;* The Parties' Proposed Procedural Schedule and Notice of Proceedings and State and Federal Litigation Pursuant to Order No. 3, Case 337-TA-1356, Exhibit 2017, (26 pages).
IPR2024-00386, *Jeisys* v. *Serendia;* Order No. 6 Adopted Procedural Schedule, Case 337-TA-1356, Exhibit 2018, (12 pages).
IPR2024-00386, *Jeisys* v. *Serendia;* Respondents' Joint Reply Post-Hearing Brief, Case 337-TA-1356, Exhibit 2019, (6 pages).
IPR2024-00386, *Jeisys* v. *Serendia;* Response of Ilooda to the Complaint and Notice of Investigation, Case 337-TA-1356, Exhibit 2020, (88 pages).
IPR2024-00386, *Jeisys* v. *Serendia;* Jeisys and Cynosure's Response to the Complaint and Notice of Investigation, Case 337-TA-1356, Exhibit 2021, (68 pages).
IPR2024-00386, *Jeisys* v. *Serendia;* Letter from Merle W. Richman to Cutera dated Mar. 20, 2018, Exhibit 2022, (1 page).
IPR2024-00386, *Jeisys* v. *Serendia;* Letter from Keith K. Im to Cynosure dated Nov. 29, 2021, Exhibit 2023, (2 pages).
IPR2024-00386, *Jeisys* v. *Serendia;* Order No. 33 Granting Parties' Joint Motion to Amend the Amended Procedural Schedule dated Oct. 19, 2023, Case 337-TA-1356, Exhibit 2024, (5 pages).
IPR2024-00386, *Jeisys* v. *Serendia;* Ex. A-02 Invalidity Claim Chart, U.S. Pat. No. 9,480,836, Case 337-TA-1356, Exhibit 2025, (65 pages).
IPR2024-00386, *Jeisys* v. *Serendia;* U.S. Pat. No. 6,766,202 B2 (Underwood), Exhibit 2026, (16 pages).
IPR2024-00386, *Jeisys* v. *Serendia;* U.S. Pat. No. 9,095,358 B2 (Woloszko), Exhibit 2027, (20 pages).
IPR2024-00386, *Jeisys* v. *Serendia;* U.S. Pat. No. 8,012,153 B2 (Woloszko), Exhibit 2028, (32 pages).
IPR2024-00386, Declaration of Daniel W. Van Der Weide in Support of Patent Owner's Preliminary Response (*Ilooda Co., Ltd and Jeisys Medical Inc.* v. *Serendia, LLC;* U.S. Pat. No. 9,480,836), Exhibit 2030 (70 pages).
IPR2024-00386, Declaration of David J. Goldberg in Support of Patent Owner's Preliminary Response (*Ilooda Co., Ltd and Jeisys Medical Inc.* v. *Serendia, LLC;* U.S. Pat. No. 9,480,836), Exhibit 2031 (36 pages).
IPR2024-00386, Na, Jongju et al., "Electromagnetic Initiation and Propagation of Bipolar Radiofrequency Tissue Reactions via Invasive Non-Insulated Microneedle Electrodes", published on Nov. 13, 2015, IPR2024-00386, Exhibit 2032, (9 pages).
IPR2024-00386, *Jeisys* v. *Serendia;* Hearing transcript held Dec. 11, 2023; Case 337-TA-1356, Exhibit 2033, (4 pages).
IPR2024-00386, *Jeisys* v. *Serendia;* U.S. Patent Appl. Publ. No. 20110288543 A1 (Cheng), Exhibit 2034, (19 pages).
IPR2024-00386, *Jeisys* v. *Serendia;* Deposition transcript of Jongju Na taken Jul. 24, 2023; Case 337-TA-1356, Exhibit 2035, (4 pages).
IPR2024-00386, *Jeisys* v. *Serendia;* Letter from Long H. Chen-S, FDA dated Jun. 17, 2022, Exhibit 2036, (10 pages).
IPR2024-00386, *Jeisys* v. *Serendia;* Brochure Sylfirm X Dual Wave RF Microneedling System, Exhibit 2037, (16 pages).
IPR2024-00386, *Jeisys* v. *Serendia;* ViOL Patent List, https://violmedical.com/about/patent; Exhibit 2038, (2 pages).
IPR2024-00386, *Jeisys* v. *Serendia;* Sylfirm X Video.mov, "A New Paradigm for RF Micro-Needling"; Exhibit 2039.
IPR2024-00386, *Jeisys* v. *Serendia;* Transcript of Exhibit 2039—Sylfirm X Video; Exhibit 2040, (1 page).
IPR2024-00386, *Jeisys* v. *Serendia;* Kevin A. Wilson, Leading Regenerative Therapies Creating a Paradigm Shift in Aesthetic Medicine; Exhibit 2042, (9 pages).
IPR2024-00386, *Jeisys* v. *Serendia;* Sylfirm X testimonials; Exhibit 2043, (1 page).
IPR2024-00386, *Jeisys* v. *Serendia;* ViOL, Sylfirm X Clinical Paper Summary; Exhibit 2044, (34 pages).
IPR2024-00386, *Jeisys* v. *Serendia;* S.B. Cho et al., In Vivo Skin Reactions from Pulsed-Type, bipolar, alternating current radiofrequency treatment using invasive noninsulated electrodes; Exhibit 2045, (8 pages).
IPR2024-00386, *Jeisys* v. *Serendia;* You Jin Jung et al., Therapeutic Effects of a new invasive pulsed-type bipolar radiofrequency for facial erythema associated with acne vulgaris and rosacea, published on Mar. 2, 2021; Exhibit 2046, (6 pages).

(56) References Cited

OTHER PUBLICATIONS

IPR2024-00386, *Jeisys v. Serendia;* Shaun Wootten et al., An Evaluation of Electrocoagulation and thermal diffusion following radiofrequency microneedling using an in vivo porcine skin model, accepted on Aug. 4, 2020; Exhibit 2047, (7 pages).

IPR2024-00386, *Jeisys v. Serendia;* Yoram Harth et al., Depressed Acne Scars—Effective, Minimal Downtime Treatment with a Novel Smooth, Motion Non-Insulated Microneedle Radiofrequency Technology, accepted on Jun. 25, 2014; Exhibit 2048, (83 pages).

IPR2024-00386, *Jeisys v. Serendia;* U.S. Pat. No. 9,510,899 B2 (Manstein), Exhibit 2049, (14 pages).

IPR2024-00386, *Jeisys v. Serendia;* U.S. Pat. No. 6,770,071 B2 (Woloszko), Exhibit 2050, (66 pages).

IPR2024-00386, *Jeisys v. Serendia;* U.S. Patent Appl. Publ. No. 20080082090 A1, Exhibit 2051, (15 pages).

IPR2024-00386, *Jeisys v. Serendia;* Respondents' Notice of Prior Art; Case 337-TA-1356, Exhibit 2053, (11 page).

IPR2024-00386, *Jeisys v. Serendia;* Curriculum Vitae of David J. Goldberg, Exhibit 2055, (22 pages).

IPR2024-00386, *Jeisys v. Serendia;* Hee Kyung Kim et al., Immediate and Late Effects of Pulse Widths and Cycles on Bipolar, Gated Radiofrequency-Induced Tissue Reactions in in vivo Rat Skin, published on Mar. 25, 2023; Exhibit 2056, (10 pages).

IPR2024-00386, *Jeisys v. Serendia;* S. Tyler et al., Radiofrequency in Cosmetic Dermatology, vol. 24, No. 12, Dec. 2011; Exhibit 2057, (10 pages).

IPR2024-00463, Patent Owner's Preliminary Response (*Jeisys Medical Inc. v. Serendia, LLC;* U.S. Pat. No. 10,869,812), May 22, 2024 (84 pages).

IPR2024-00463, Patent Owner Motion To Seal (*Jeisys Medical Inc. v. Serendia, LLC;* U.S. Pat. No. 10,869,812), May 22, 2024 (9 pages).

IPR2024-00463, *Jeisys v. Serendia;* Complainant's Jul. 24, 2023 Supplemental Validity Contentions, Case 337-TA-1356, Exhibit 2003, (425 pages).

IPR2024-00463, *Jeisys v. Serendia;* Expert Report of Jean Woloszko, Case 337-TA-1356, Exhibit 2004, (684 pages).

IPR2024-00463, *Jeisys v. Serendia;* Deposition transcript of Jean Woloszko taken Sep. 14, 2023, Case 337-TA-1356, Exhibit 2007, (2 pages).

IPR2024-00463, *Jeisys v. Serendia;* Deposition transcript of Jean Woloszko taken Sep. 15, 2023, Case 337-TA-1356, Exhibit 2008, (2 pages).

IPR2024-00463, *Jeisys v. Serendia;* Complainant's Public Interest Statement & Complaint of Serendia, Case 337-TA-_, Exhibit 2016, (74 pages).

IPR2024-00463, *Jeisys v. Serendia;* The Parties' Proposed Procedural Schedule and Notice of Proceedings and State and Federal Litigation Pursuant to Order No. 3, Case 337-TA-1356, Exhibit 2017, (26 pages).

IPR2024-00463, *Jeisys v. Serendia;* Order No. 6 Adopted Procedural Schedule, Case 337-TA-1356, Exhibit 2018, (12 pages).

IPR2024-00463, *Jeisys v. Serendia;* Respondents' Joint Reply Post-Hearing Brief, Case 337-TA-1356, Exhibit 2019, (6 pages).

IPR2024-00463, *Jeisys v. Serendia;* Jeisys and Cynosure's Response to the Complaint and Notice of Investigation, Case 337-TA-1356, Exhibit 2021, (68 pages).

IPR2024-00463, *Jeisys v. Serendia;* Letter from Keith K. Im to Cynosure dated Nov. 29, 2021, Exhibit 2023, (2 pages).

IPR2024-00463, *Jeisys v. Serendia;* Order No. 33 Granting Parties' Joint Motion to Amend the Amended Procedural Schedule dated Oct. 19, 2023, Case 337-TA-1356, Exhibit 2024, (5 pages).

IPR2024-00463, *Jeisys v. Serendia;* Brochure Sylfirm X Dual Wave RF Microneedling System, Exhibit 2037, (16 pages).

IPR2024-00463, *Jeisys v. Serendia;* Respondents' Notice of Prior Art; Case 337-TA-1356, Exhibit 2053, (11 page).

IPR2024-00463, *Jeisys v. Serendia;* Sylfirm X Revolutionizes Clinical Applications of RF Microneedling dated May/ Jun. 2022, Exhibit 2066, (3 pages).

IPR2024-00463, *Jeisys v. Serendia;* World-Class Product of Korea 2020 Certificate to ViOL (Dec. 9, 2020); Exhibit 2067, (1 page).

IPR2024-00463, *Jeisys v. Serendia;* Vincent A. Thomas CV; Exhibit 2070, (17 pages).

IPR2024-00463, *Jeisys v. Serendia;* ViOL, Sylfirm X User Manual; Exhibit 2083, (43 pages).

IPR2024-00463, *Jeisys v. Serendia;* Sylfirm X Product Photographs; Exhibit 2086, (11 pages).

IPR2024-00463, *Jeisys v. Serendia;* Sylfirm X Introduction Video 1.mp4, "New X Tips"; Exhibit 2097.

IPR2024-00463, *Jeisys v. Serendia;* Transcript of Sylfirm X Introduction Video 1; Exhibit 2098, (1 page).

IPR2024-00463, *Jeisys v. Serendia;* Deposition Transcript of Peter Crosby taken Sep. 4, 2023, Case 337-TA-1356, Exhibit 2103, (2 pages).

IPR2024-00463, *Jeisys v. Serendia;* Deposition Transcript of Peter Crosby taken Sep. 5, 2023, Case 337-TA-1356, Exhibit 2104, (2 pages).

IPR2024-00463, *Jeisys v. Serendia;* U.S. Patent Application Publication No. 20020120260 A1, Exhibit 2108, (67 pages).

IPR2024-00463, *Jeisys v. Serendia;* Certified English translation of Korean Registered Patent Publication No. KR10-0852500, Exhibit 2110, (11 pages).

IPR2024-00463, *Jeisys v. Serendia;* Respondents' Amended Notice of Prior Art, Case 337-TA-1356, Exhibit 2111, (11 pages).

IPR2024-00463, *Jeisys v. Serendia;* USPTO File History for U.S. Pat. No. 9,320,536, Exhibit 2114, (362 pages).

IPR2024-00463, *Jeisys v. Serendia;* U.S. Pat. No. 6,890,319 B1, Exhibit 2115, (18 pages).

IPR2024-00463, *Jeisys v. Serendia;* U.S. Pat. No. 6,277,116 B1, Exhibit 2119, (22 pages).

IPR2024-00463, *Jeisys v. Serendia;* U.S. Patent Application Publication No. 20020120261 A1, Exhibit 2120, (62 pages).

IPR2024-00463, *Jeisys v. Serendia;* Cartessa Aesthetics, Innovation in RF Microneedling: A closer look at VirtueRF, Jun. 2021, Exhibit 2122, (4 pages).

IPR2024-00463, *Jeisys v. Serendia;* Woloszko Hearing Transcript dated Nov. 7, 2023, Case 337-TA-1356, Exhibit 2125, (69 pages).

IPR2024-00463, *Jeisys v. Serendia;* Crosby Hearing Transcript dated Dec. 12, 2023, Case 337-TA-1356, Exhibit 2126, (31 pages).

IPR2024-00463, *Jeisys v. Serendia;* Sylfirm X—Product Inspection Report, Appendix 17, Case 337-TA-1356, Exhibit 2127, (11 pages).

IPR2024-00463, *Jeisys v. Serendia;* Deposition transcript of Jongju Na dated Jul. 25, 2023, Case 337-TA-1356, Exhibit 2128, (5 pages).

IPR2024-00463, *Jeisys v. Serendia;* Sylfirm X Product Photographs, Exhibit 2130, (4 pages).

IPR2024-00463, *Jeisys v. Serendia;* U.S. Patent Application Publication No. 20060036210 A1, Exhibit 2132, (69 pages).

IPR2024-00463, *Jeisys v. Serendia;* Peter Crosby CV, Exhibit 2136, (8 pages).

IPR2024-00463, *Jeisys v. Serendia;* Appendix 7—U.S. Pat. No. 10,869,812 Patent Summary Invalidity Claim Chart, Exhibit 2139, (7 pages).

IPR2024-00463, Declaration of Peter Crosby in Support of Patent Owner's Preliminary Response, (*Jeisys Medical Inc. v. Serendia, LLC;* U.S. Pat. No. 10,869,812), Exhibit 2140 (69 pages).

IPR2024-00463, Declaration of Vince Thomas in Support of Patent Owner's Preliminary Response, (*Jeisys Medical Inc. v. Serendia, LLC;* U.S. Pat. No. 10,869,812), Exhibit 2141 (8 pages).

IPR2024-00463, *Jeisys v. Serendia;* U.S. Patent Application Publication No. 20040058882 A1, Exhibit 2142, (26 pages).

IPR2024-00463, *Jeisys v. Serendia;* U.S. Patent Application Publication No. 20080091182 A1, Exhibit 2143, (35 pages).

IPR2024-00463, *Jeisys v. Serendia;* USPTO Statutory Disclaimer dated May 13, 2024, U.S. Appl. No. 15/724,261, Exhibit 2144, (6 pages).

\* cited by examiner

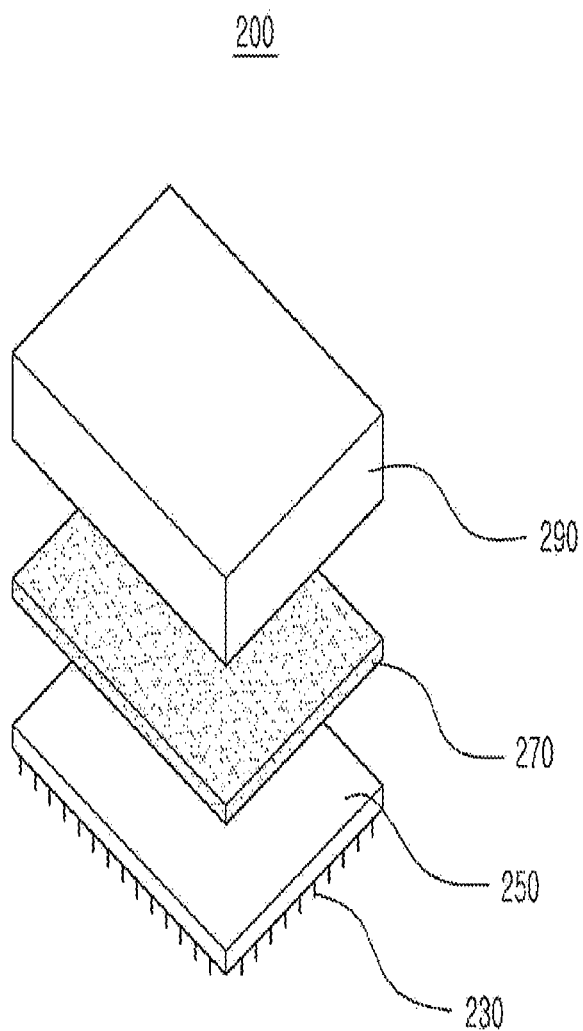
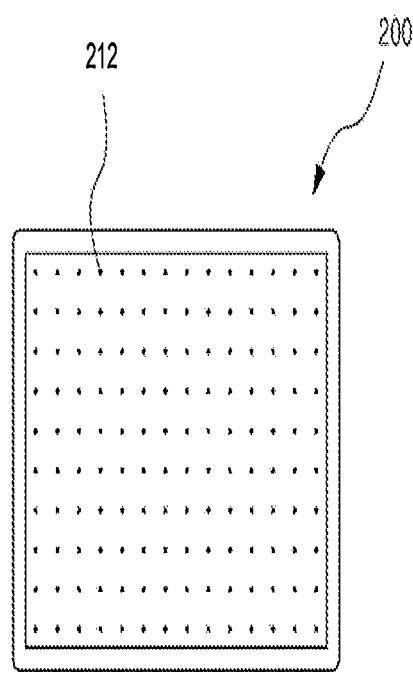
FIGURE 1C
FIGURE 1D

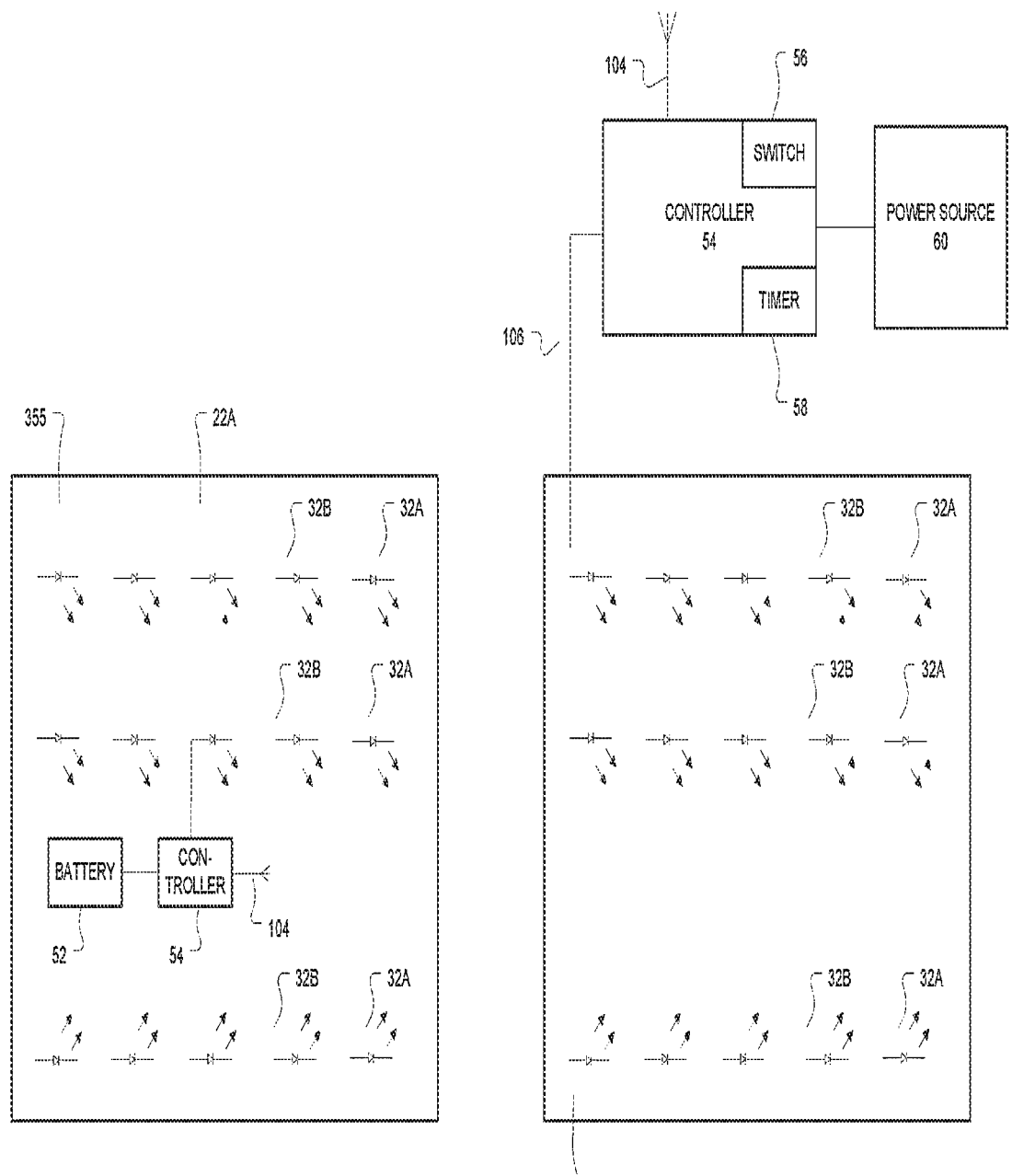
FIGURE 4A    520        FIGURE 4B    510

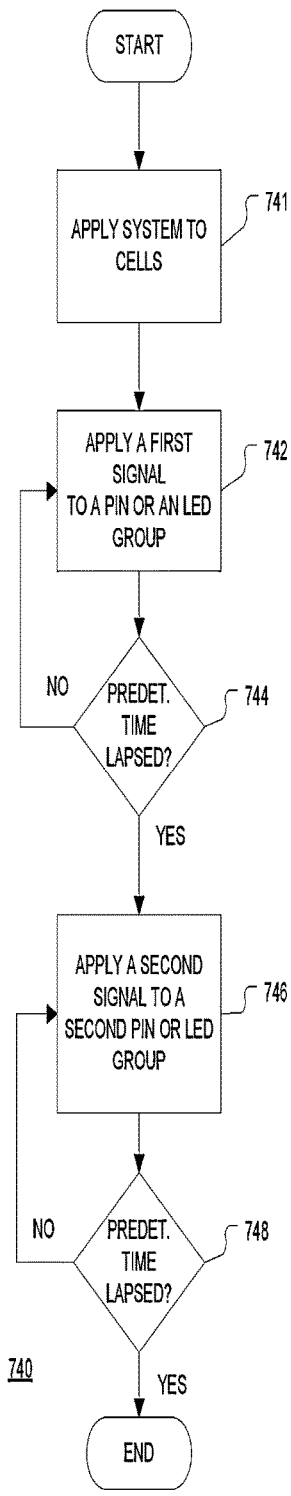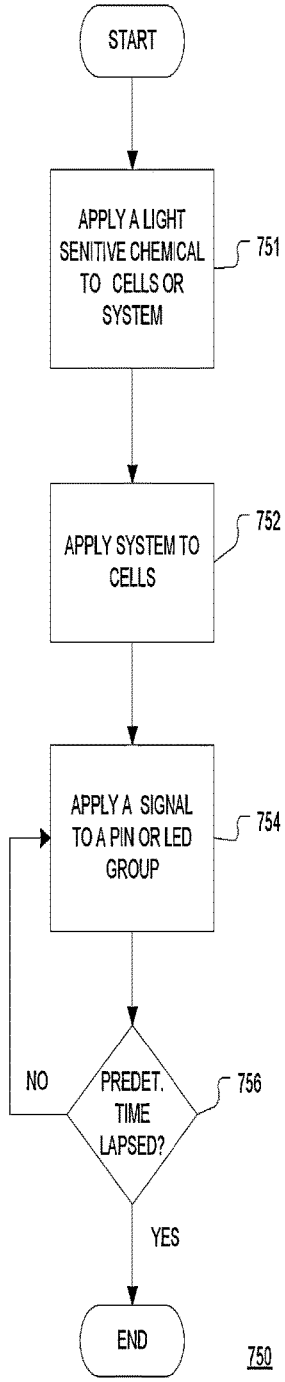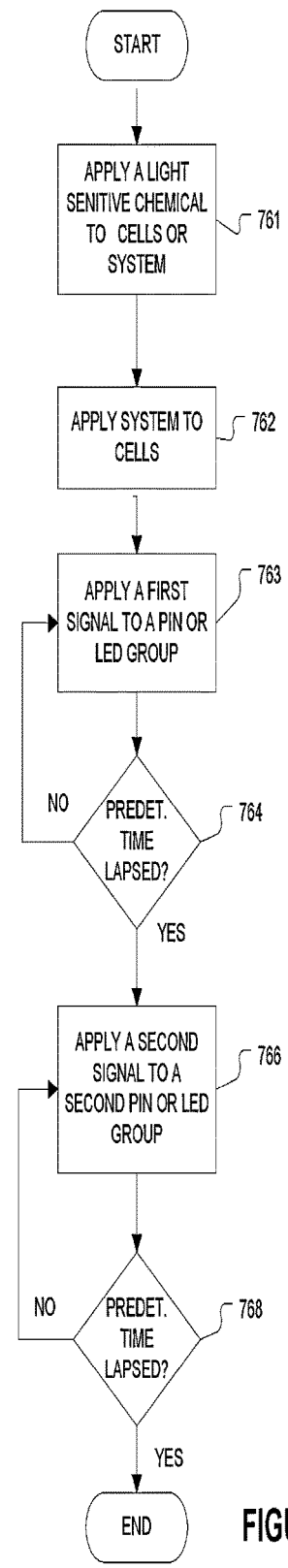
FIGURE 7A
FIGURE 7B
FIGURE 7C

US 12,220,549 B2

METHOD, SYSTEM, AND APPARATUS FOR DERMATOLOGICAL TREATMENT

CROSS REFERENCE TO RELATED APPLICATIONS

The present application is a continuation of U.S. application Ser. No. 17/131,711, entitled "METHOD, SYSTEM, AND APPARATUS FOR DERMATOLOGICAL TREATMENT", filed on Dec. 22, 2020, which is a continuation of U.S. application Ser. No. 15/724,261, entitled "METHOD, SYSTEM, AND APPARATUS FOR DERMATOLOGICAL TREATMENT", filed on Oct. 3, 2017, now U.S. Pat. No. 10,869,812, which is a continuation of U.S. application Ser. No. 15/096,686, entitled "METHOD, SYSTEM, AND APPARATUS FOR DERMATOLOGICAL TREATMENT", filed on Apr. 12, 2016, now U.S. Pat. No. 9,775,774, which is a continuation of U.S. application Ser. No. 13/825,083, entitled "METHOD, SYSTEM, AND APPARATUS FOR DERMALOGICAL TREATMENT", filed on Jan. 20, 2014 now U.S. Pat. No. 9,320,536, which is a National Stage entry of PCT/KR2012/001335, filed on Feb. 22, 2012, which claims priority to U.S. Application No. 61/449,080, entitled "METHOD, SYSTEM, AND APPARATUS FOR DERMALOGICAL TREATMENT", filed on Mar. 3, 2011 and U.S. application Ser. No. 13/060,274, U.S. Pat. No. 8,979,912, entitled "METHOD, SYSTEM, AND APPARATUS FOR DERMALOGICAL TREATMENT", filed on Feb. 22, 2011, the entirety of each is incorporated by reference.

TECHNICAL FIELD

Various embodiments described herein relate generally to treating dermatological tissue, including systems, and methods used in treating dermatological tissue.

BACKGROUND INFORMATION

It may be desirable to treat dermatological tissue; the present invention provides such treatment.

BRIEF DESCRIPTION OF THE DRAWINGS

FIG. 1C is a simplified, exploded layer view of the dermatological treatment apparatus according to various embodiments.

FIG. 1D is a simplified view of a layer of a dermatological treatment apparatus according to various embodiments.

FIG. 4A is a simplified view of a layer of a dermatological treatment apparatus according to various embodiments.

FIG. 4B is a simplified view of a layer and apparatus of a dermatological treatment system according to various embodiments.

FIG. 7A-7C are flow diagrams illustrating dermatological treatment system processing algorithms according to various embodiments.

DETAILED DESCRIPTION

Figure 1A:
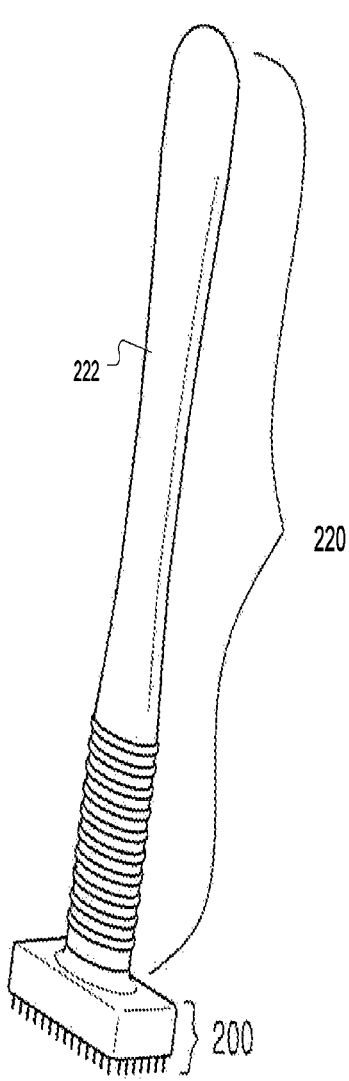
FIG. 1A is a simplified isometric diagram of a dermatological treatment apparatus according to various embodiments.
Figure 1B:
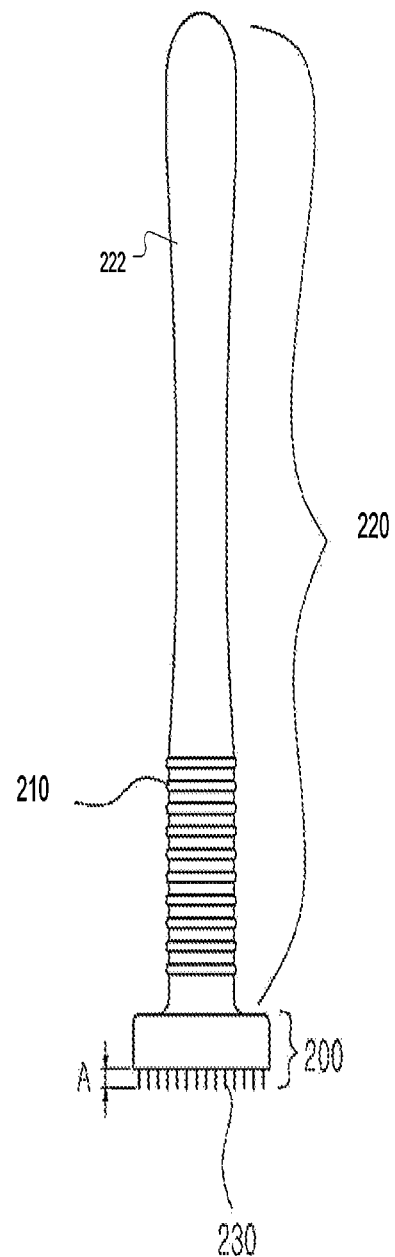
FIG. 1B is a simplified, side diagram of the dermatological treatment apparatus according to various embodiments.

FIG. 1A is a simplified isometric diagram and FIG. 1B is a simplified side view of a dermatological treatment apparatus 10 according to various embodiments. The apparatus 10 may include a user handle 220 coupled to an acupuncture plate 200. In an embodiment the plate 200 may be elastically coupled to the handle segment 222 via an elastomeric section 210. The elastomeric section may be comprised of a combination of elastomeric materials and non-elastomeric materials. The elastomeric materials may include plastics, rubber (synthetic or natural), and spring(s).

FIG. 1C includes a simplified exploded view of an embodiment of an acupuncture plate 200 according to various embodiments. The plate 200 may include an upper, substantially rigid section or layer 290, deformable or elastic section 270 or layer, and acupuncture section or layer 250. The acupuncture section 250 may include a plurality of acupuncture pins or needles 230. FIG. 1D is a simplified bottom view of the plate 200 showing the location or holes 212 for the pins or needles 230. In an embodiment the plate 200 may have a rectangular cross section having a dimensional about 1 to 4 cm in width and about 1 to 6 cm in length. The plate 200 may any shape including circular, elliptical, polygon, or other shape where the shape may be particular to a dermatological area to be treated.

In an embodiment the plate may include about 140 pins or needles 230 uniformly separated. Each needle may be about 0.1 to 0.4 mm in diameter and 0.2 mm to 1.4 mm in length including 0.3 mm diameter and 0.8 mm in length in an embodiment. The elastic section or layer 270 may be comprised of a combination of elastomeric materials and non-elastomeric materials. The elastomeric materials may include plastics, rubber (synthetic or natural), and spring(s). The pin section 250 may be coupled directly or indirectly to the upper section 290 via the elastic section 270, including via glues, screws, welds, or other connection. In an embodiment the pin section 250 may include elastomers to enable at least partial deformation of the pin section 250 about the pins 230.

In operation a user may employ the apparatus 10 to create a plurality of micro-wounds or holes in dermatological layers of a mammal's 20 skin or dermis. The micro-wound or hole creation may improve the absorption or application of one or more chemicals applied on or about the micro-wounds or holes.

Figure 2A:
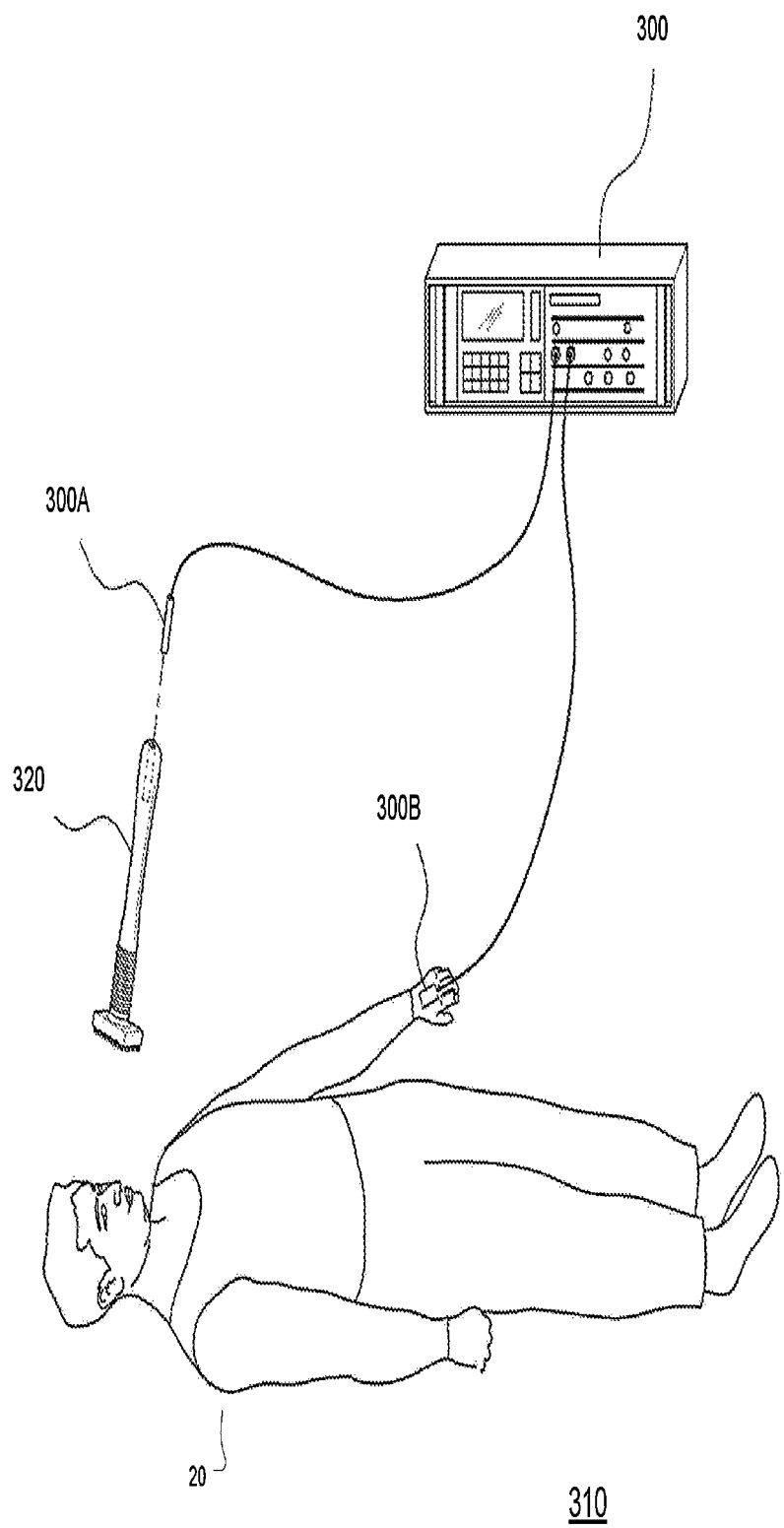
FIG. 2A is a simplified isometric diagram of a dermatological treatment architecture according to various embodiments.
Figure 2B:
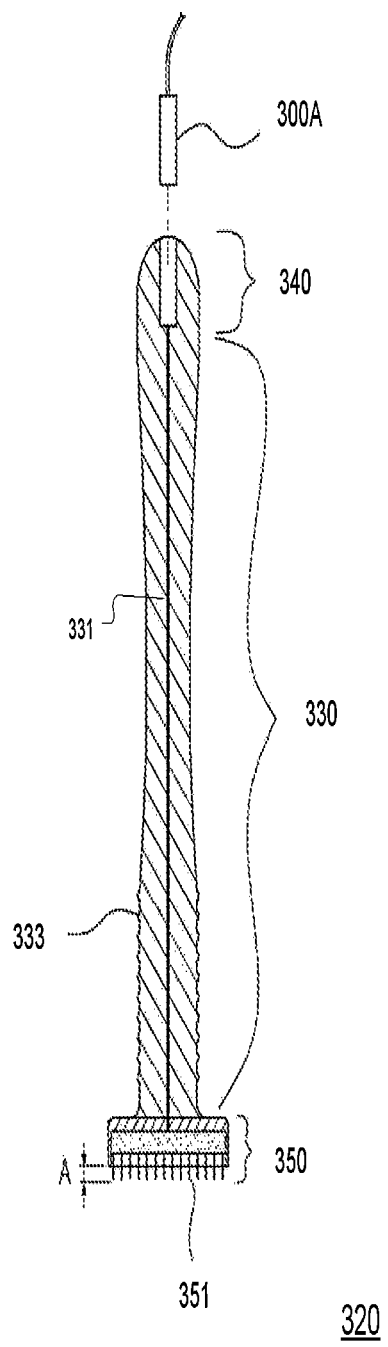
FIG. 2B is a simplified cross-sectional diagram of a dermatological treatment apparatus according to various embodiments.

FIG. 2A is a simplified diagram of a dermatological treatment architecture 310 according to various embodiments. Architecture 310 includes an acupuncture apparatus 320 and an electrical signal generation system 300. The electrical signal generation system 300 may be electrically coupled to the acupuncture apparatus 320 via one or more wires 300A and to a mammal 20 to be treated via one or more wires 300B. FIG. 2B is a simplified cross-sectional diagram of the acupuncture apparatus 320 according to various embodiments. The apparatus 320 may include a handle 330, elastic section 333, electrical interface 340, internal wire(s) 331 and plate 350. The pins 351 may have a length A (0.3 mm to 2.1 mm in an embodiment) where at least one pin 351 is electrically coupled to the electrical interface 340 via the internal wire 331. The electrical interface 340 may be removably connected to the system 300 wire 300A.

Figure 2C:
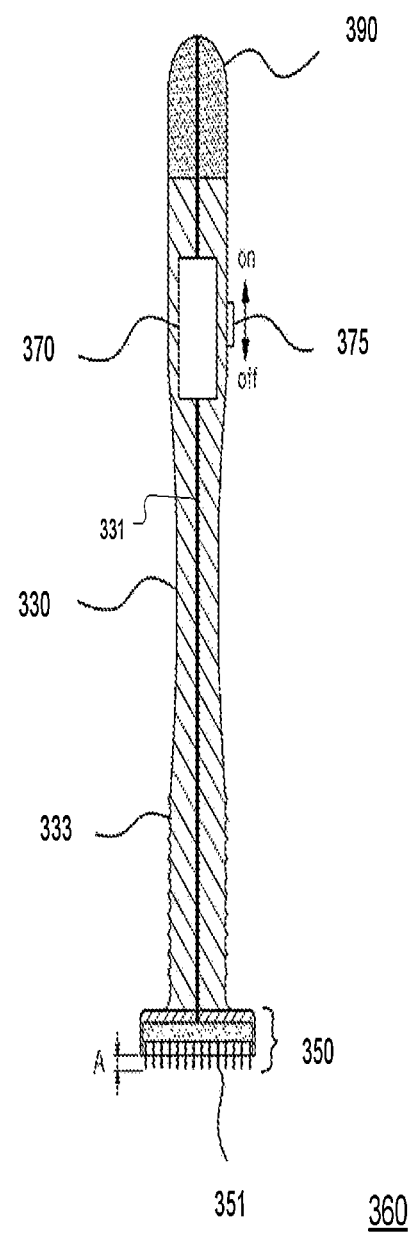
FIG. 2C is a simplified cross-sectional diagram of another dermatological treatment apparatus according to various embodiments.
Figure 5A:
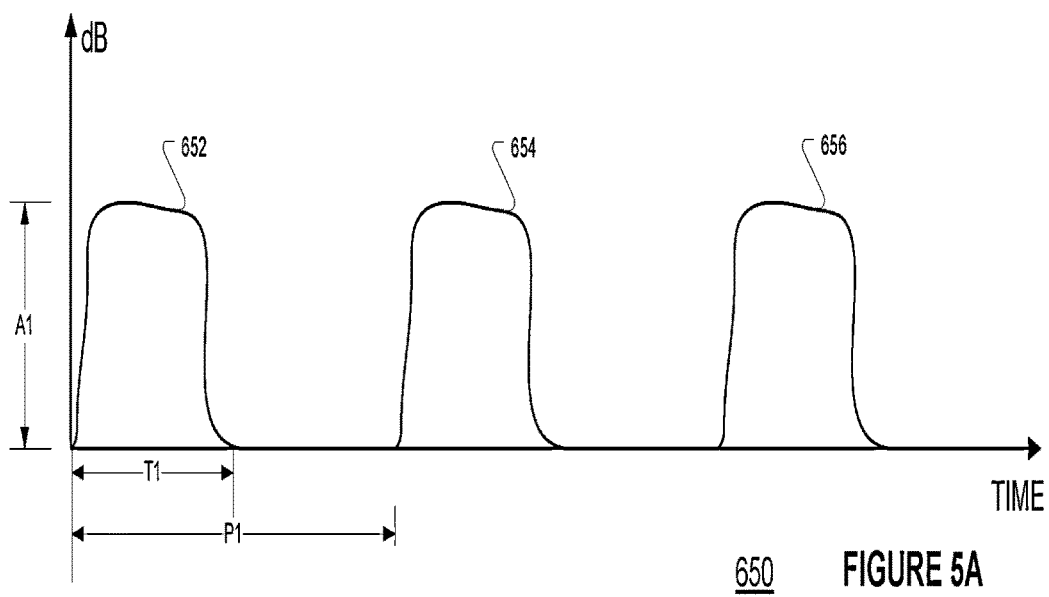
FIGS. 5A-6 are diagrams of signals that may be applied to one or more dermatological treatment systems according to various embodiments.
Figure 5B:
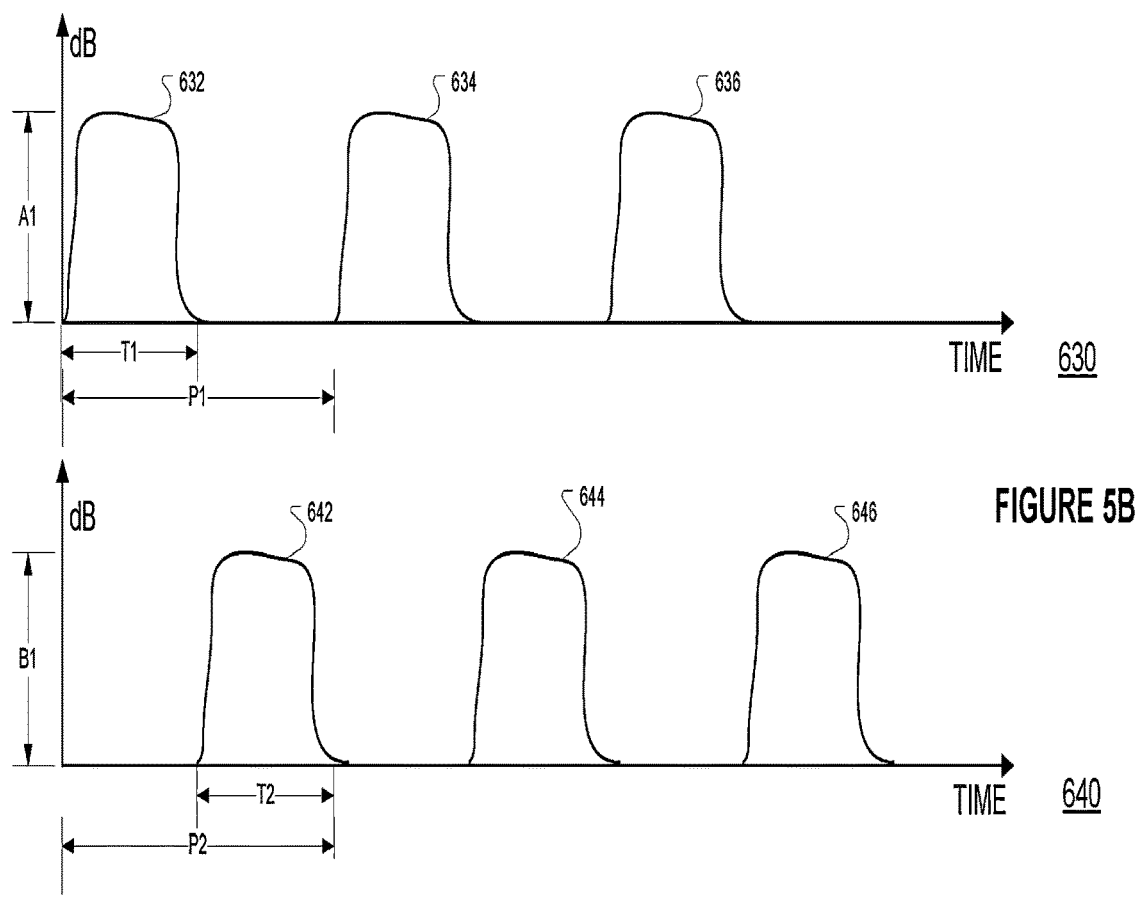
Figure 6:
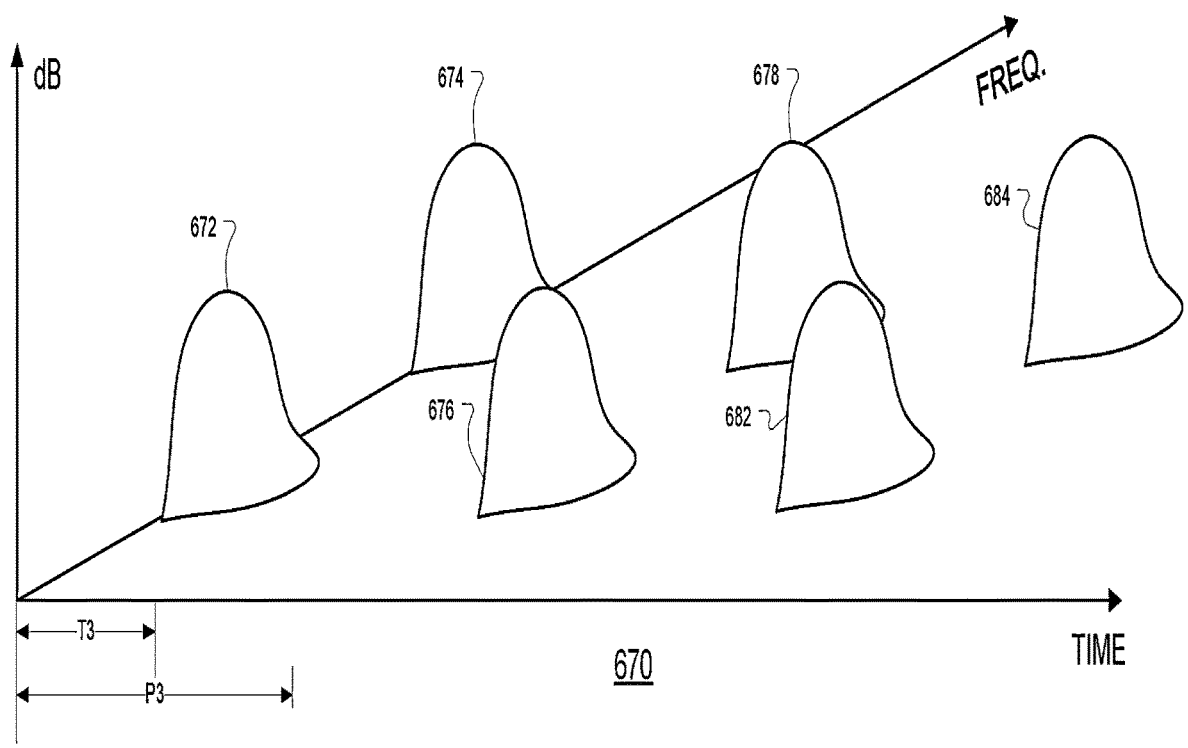

The electrical signal generation system 300 may generate a variety of signals (such as shown in FIGS. 5A to 6) to vibrate one or more pins 351 electrically coupled to the system 300 via the internal wire 331 and lead 300A. A pin vibration 351 may increase the micro-wound or cut formed in dermis by the pin 351. FIG. 2C is a simplified cross-sectional diagram of an acupuncture apparatus 360 according to various embodiments. The apparatus 360 may include a handle 330, an elastic section 333, an electrical conductive interface 390, internal wire(s) 331, signal generator 370, switch 375, and plate 350. The signal generator 370 may be coupled to at least one pin 351 via internal wire 331 and coupled to the conductive interface 390.

The signal generator or module 370 may generate a variety of signals (such as shown in FIGS. 5A to 6) to vibrate one or more pins 351 electrically coupled to the system 300 via the internal wire 331 and the conductive interface 390. In operation a user 20 may touch the conductive interface 390 and place one or more electrically coupled pins 351 in contact with their dermis to form an electrical pathway from the pin 351 to the electrical conductive interface 390. The signal generator 370 may include a battery to supply energy to generate one or more electrical signals. The switch 375 coupled to the generator 370 may cause the generator to produce one or more electrical signals for a predetermined time interval or until the switch 375 is triggered again. As noted a pin vibration 351 may increase the micro-wound or cut formed in dermis by the pin 351.

Figure 2D:
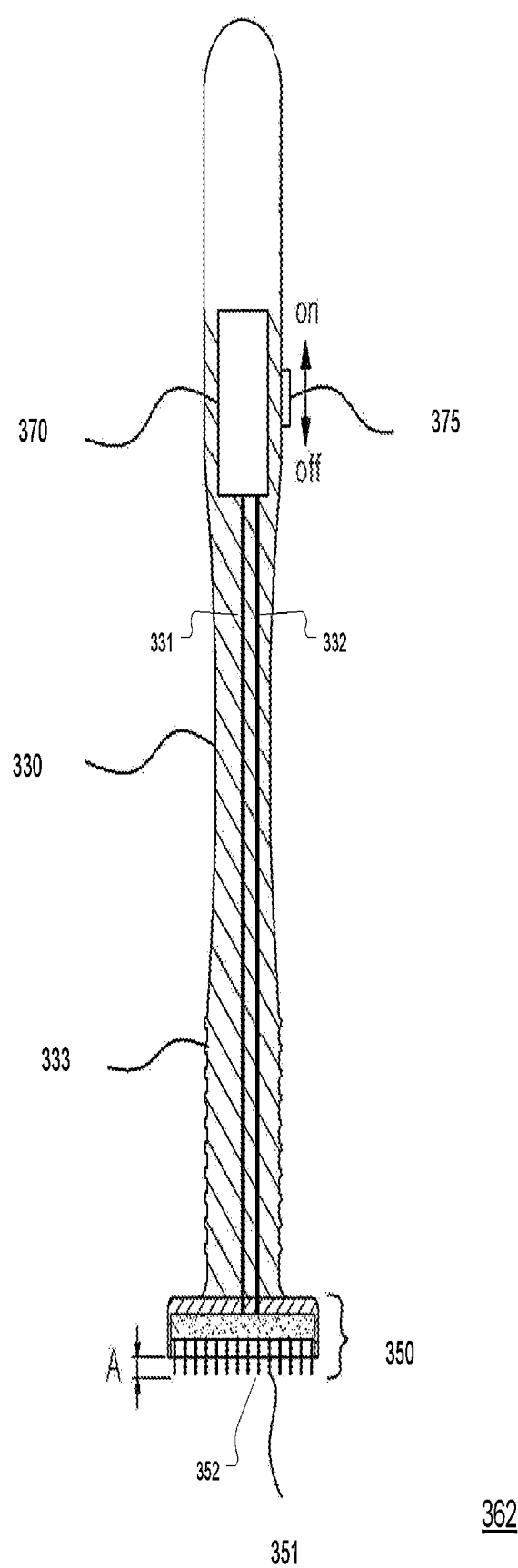
FIG. 2D is a simplified cross-sectional diagram of another dermatological treatment apparatus according to various embodiments.
Figure 2E:
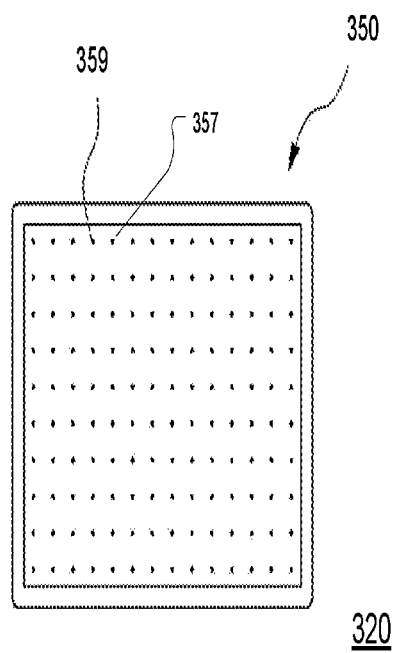
FIG. 2E is a simplified view of a layer of a dermatological treatment apparatus according to various embodiments.

FIG. 2D is a simplified cross-sectional diagram of an acupuncture apparatus 362 according to various embodiments. The apparatus 362 may include a handle 330, an elastic section 333, internal wire(s) 331, 332, signal generator 370, switch 375, and plate 350. The signal generator 370 may be coupled to at least one pin 351 via internal wire 331 and coupled to at least one other pin 352 via internal wire 332. When active the pins 351, 352 may form at least one dipole pair. The signal generator or module 370 may generate a variety of signals (such as shown in FIGS. 5A to 6) to vibrate one or more dipole pair or bipolar pins 351, 352.

Figure 2F:
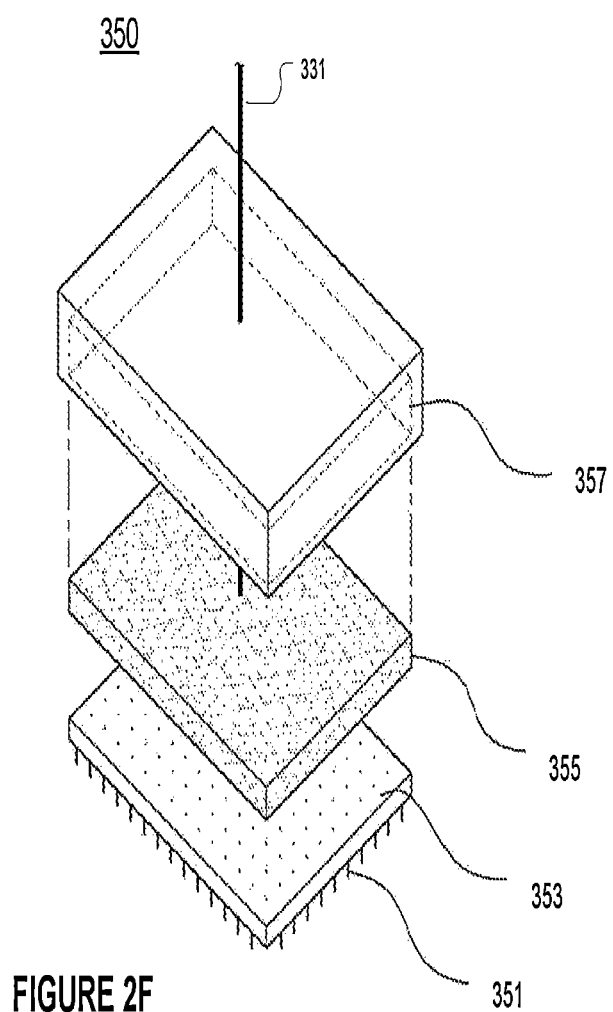
FIG. 2F is a simplified, exploded view of layers of the dermatological treatment apparatus according to various embodiments.

FIG. 2F includes a simplified exploded view of an embodiment of an acupuncture plate 350 including at least one electrically coupled pin 351 according to various embodiments. The plate 350 may include an upper, substantially rigid section or layer 357, deformable or elastic section 355 or layer, and acupuncture section or layer 353. The acupuncture section 353 may include a plurality of acupuncture pins or needles 351 where at least one pin 351 is electrically coupled to the wire 331. In a bipolar configuration a second wire 332 may be coupled to at least one other pin 351. FIG. 2F is a simplified bottom view of the plate 350 showing the pins or needles 359, 357 where the pins may be electrically coupled to a first wire 331 and a second wire 332 to form dipole pair (bipolar pins).

In an embodiment the plate 350 may have a rectangular cross section having a dimensional about 1 to 4 cm in width and about 1 to 6 cm in length. The plate 350 may any shape including circular, elliptical, polygon, or other shape where the shape may be particular to a dermatological area to be treated.

In an embodiment the plate may include about 140 pins or needles 351 uniformly separated. Each needle may be about 0.1 to 0.4 mm in diameter and 0.2 mm to 1.4 mm in length including 0.3 mm diameter and 0.8 mm in length in an embodiment. The elastic section or layer 355 may be comprised of a combination of elastomeric materials and non-elastomeric materials. The elastomeric materials may include plastics, rubber (synthetic or natural), and spring(s). The pin section 353 may be coupled directly or indirectly to the upper section 357 via the elastic section 355, including via glues, screws, welds, or other connection. In an embodiment the pin section 353 may include elastomers to enable at least partial deformation of the pin section 353 about the pins 351.

Figure 3A:
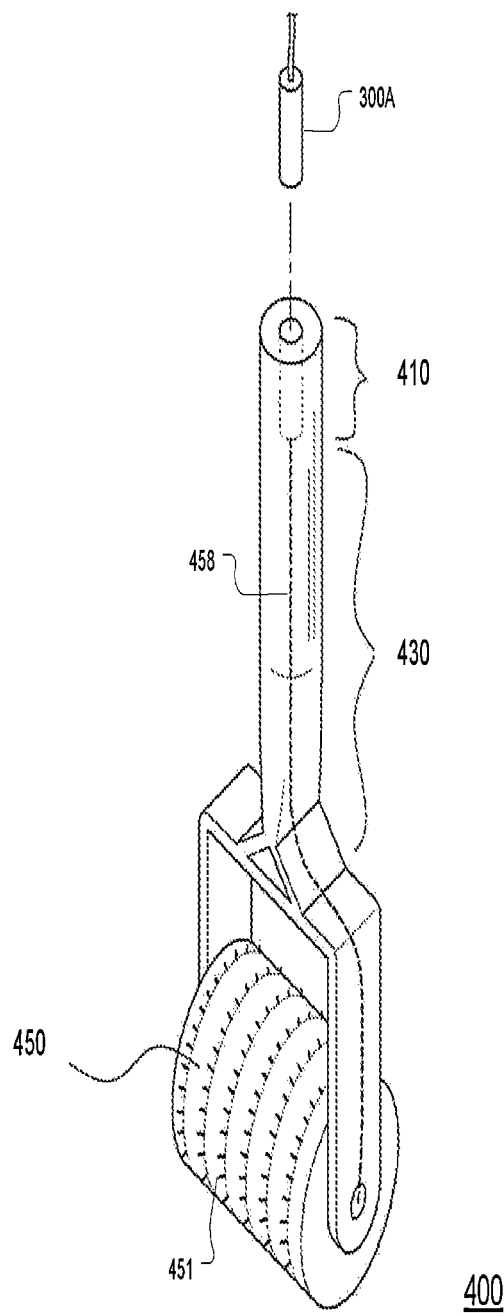
FIG. 3A is a simplified isometric diagram of a dermatological treatment apparatus according to various embodiments.
Figure 3B:
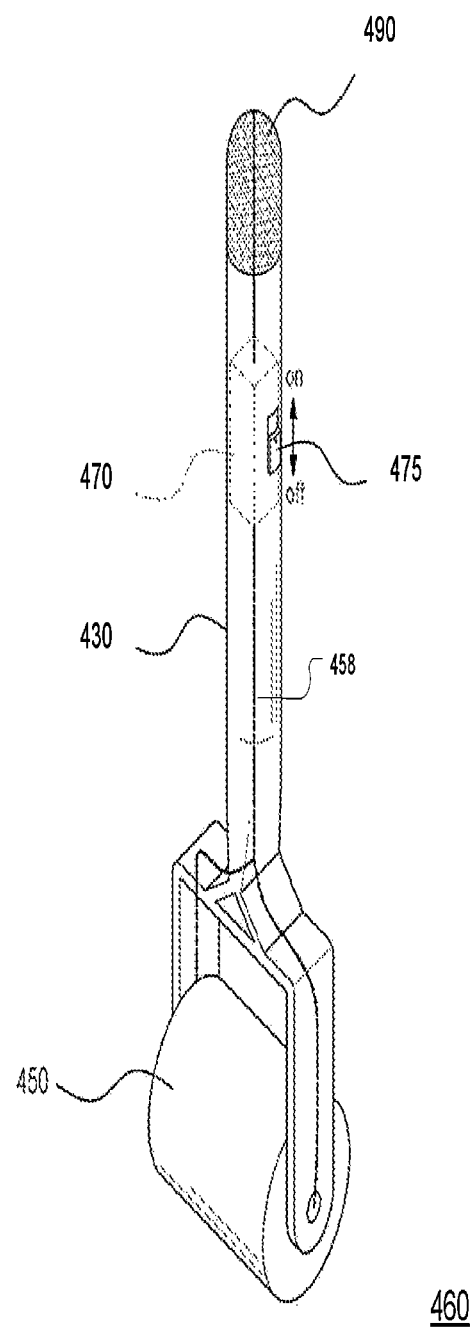
FIG. 3B is a simplified isometric diagram of another dermatological treatment apparatus according to various embodiments.

FIGS. 3A and 3B are simplified isometric diagrams of acupuncture apparatus 400, 460 including at least one pin 451 that may be coupled to an electrical signal via an internal wire 458. Each apparatus 400, 460 includes curved roller 450 having a plurality of acupuncture pins 451 where the pins 451 may be similar to pins 351. In apparatus 400, the electrical lead wire 300A may be coupled to an electrical interface 410 in the apparatus handle 430 where the interface 410 is electrically coupled to the internal wire 458. In apparatus 460, the handle 430 may include a signal generator 470 similar to generator 370, switch 475, and conduction surface 490. Apparatus 460 may operate similar to apparatus 360 in operation other than the rolling capability of the apparatus 460, 400. In an embodiment the rollers 450 may have various configurations to conform to a dermal area to be treated.

In any of the above apparatus 10, 320, 350, 360, 400, 460, the plate or roller 200, 350, 450 may include a plurality of embedded LEDs 32A, 32B, a battery 52, a controller 54, and an antenna 56 as shown in FIG. 4A. In an embodiment the LED 32A may be configured to emit energy of a first particular frequency range and the LED 32B may be configured to emit energy of a second particular frequency range. The surface 22 of a roller 450, plate 200, 350, 450 may also be embedded with a chemical 22A that may be used to treat dermatological cells. The chemical 22A may be reactive to the first and the second frequency ranges. Further dermatological cells may be reactive to the first and the second frequency ranges. In addition, the combination of the chemical 22A and the application of the first and the second frequency ranges to the chemical 22A and dermatological cells may have a synergetic effect.

In an embodiment the chemical 22A may be applied directly to the dermatological cells to be treated. In a further embodiment a chemical 22A may not be employed in addition to the apparatus 10, 320, 350, 360, 400, 460. In an embodiment the pin section 250, 353, may be translucent and comprised of polyurethane, medical silicon, or other pliable, translucent, hypoallergenic material.

In an embodiment the local controller 54 and battery 52 may also be embedded in the upper section 290, 357, pin section 230, 351, or the handle 220, 330, or separately between these sections. The controller 54 may be electrically coupled to the one or more LEDs 32A, 32B. The controller 54 may also be coupled to a battery 52. The controller 54 may generate one or more signals for LEDs 32A, 32B as a function of a user switch 75, 56. The signals may vary as a function of the first and second frequency ranges. The controller 54 may include one or more timers 58 that may limit the application of energy to the LEDs 32A, 32B to predetermined time intervals. In an embodiment the controller may also be coupled to an antenna 56 to receive or transmit one or more signals related to the transmission of energy to one or more LEDs 32A, 32B. In an embodiment the system 10 may be configured to treat a particular segment of dermatological cells such as a face. The apparatus 10 may be configured to conform to a user's anatomy so that emitted light is focused on dermatological cells. In another embodiment 200, the system 200 may be configured to treat another anatomical region including dermatological cells on an arm, leg, chest, hands, feet, neck, or other region.

In an embodiment 510 shown in FIG. 4B, a controller 54, an antenna 104, and a power source 60 may be located external to the apparatus 10, 320, 360. The power source 60 may be coupled to the controller 54. The controller 54 may be coupled to one or more LEDs 32A, 32B via one or more electric wires 106. The controller 54 may generate one or more signals for LEDs 32A, 32B as a function of the user switch 56. The signals may vary as a function of the first and second frequency ranges. The controller 54 may include one or more timers 58 that may limit the application of energy to the LEDs 32A, 32B to predetermined time intervals. In an embodiment the controller may also be coupled to an antenna 104 to receive or transmit one or more signals related to the transmission of energy to one or more LEDs 32A, 32B.

Figure 4C:
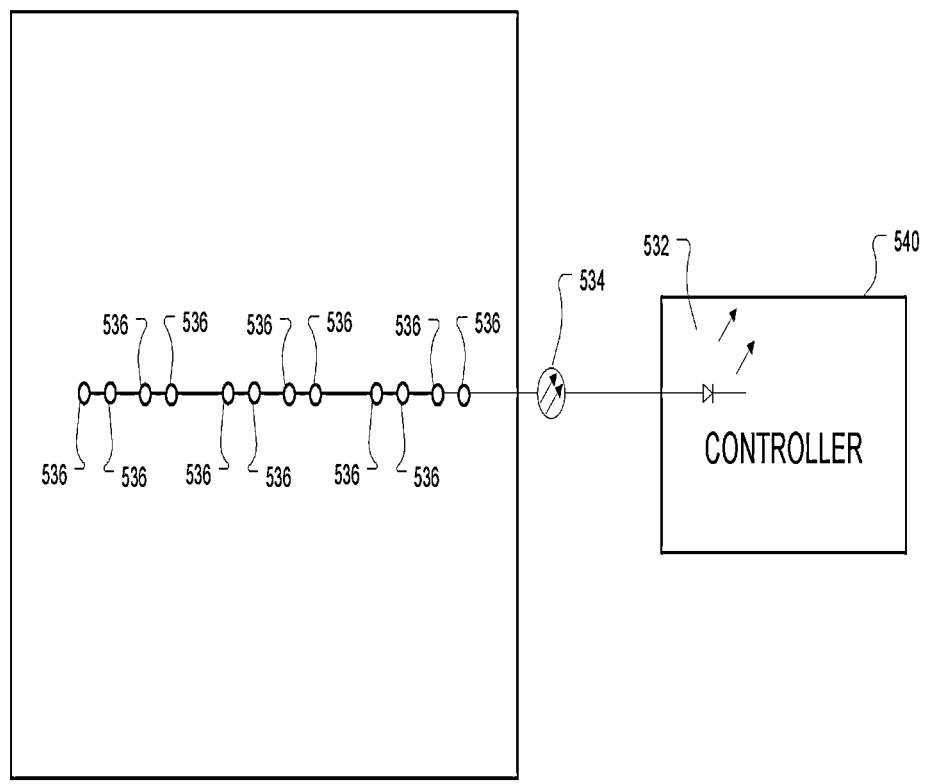
FIG. 4C is a simplified view of a layer and apparatus of a dermatological treatment system according to various embodiments.

As shown in FIG. 4C, in any of the above apparatus 10, 320, 350, 360, 400, 460, the plate or roller 200, 350, 450 may include a plurality of embedded LED lens 536, a fiber optic pathway 534, and an LED 532. In this embodiment, system 530 LED 532 shown in FIG. 4C may be coupled to lens 536 via the fiber optic pathway 534. The controller 540 may generate an LED signal via the LED 532 that is transmitted to dermatological cells via the lens 536 and the fiber optic pathway 534.

FIGS. 5A-5B are diagrams of electrical signal waveforms 650, 630, 640 that may be applied to one or more LEDs 32A, 32B, 532 and to the pins 230, 351, 451 according to various embodiments. The signal waveform 650 includes several square-wave pulses 652, 654, 656 that may be applied to an LED 32A, 32B, 532. Each pulse 652, 654, 656 may a have a similar magnitude and envelope. The waveform 650 may be used to energize an LED 32A, 32B, 532 and to the pins 230, 351, 451 periodically P1 for a predetermined interval T1 where each pulse 652, 654, 656 has a amplitude A1. In an embodiment, A1 may be about 0.1 milliamperes (mA) to 10 mA, the pulse width T1 may be about 100 microseconds (μs) to 500 μs and the period P1 may from 100 ms to 500 ms as a function of the energy required to create capacitance in a liquid. In another embodiment, A1 may be about 0.5 milliamperes (mA) to 5 mA, the pulse width T1 may be about 200 microsecond (μs) and the period P1 may about 250 ms as a function of the energy to drive an LED or cause one or more pins 230, 351, 451 to vibrate.

In FIG. 5B a signal waveform 630 may be applied to a first LED 32A, 32B, 532 module or group and to the pins 230, 351, 451 and a second waveform 640 may be applied or used to energize a second LED 32A, 32B, 532 module and the pins 230, 351, 451, 352. The signal waveform 630 includes several square-wave pulses 632, 634, and 636 and the signal waveform 640 includes several square-wave pulses 642, 644, and 646. Each pulse 632, 634, 636, 642, 644, 646 may a have a similar magnitude and envelope. The waveform 630 may be used to energize a first LED 32A, 32B, 332 module and the pins 230, 351, 451 periodically P1 for a predetermined interval T1 where each pulse 632, 634, 636 has an amplitude A1. The waveform 640 may be used to energize a second LED 32A, 32B, 332 module and the pins 230, 351, 451 periodically P2 for a predetermined interval T2 where each pulse 642, 644, 646 has an amplitude B1. The pulse width T1, T2 may be about 100 microseconds (μs) to 500 μs and the period P1, P2 may from 100 ms to 500 ms as a function of the energy to affect dermatological cells or chemicals 22A. In another embodiment, A1, A2 may be about 0.5 milliamperes (mA) to 5 mA, the pulse width T1, T2 may be about 200 microsecond (μs) and the period P1, P2 may about 250 ms as a function of the energy required to affect dermatological cells or chemicals 22A. In an embodiment the pulses 632, 634, 636 do not substantially overlap the pulses 642, 644, 646. In an embodiment T1>T2 and P2 is an integer multiple of P1.

FIG. 6 depicts a waveform 670 that includes multiple pulses 672, 674, 676, 678, 682, and 684 that may not overlap in the time or the frequency domain. In an embodiment each pulse 672, 674, 676, 678, 682, and 684 may have a pulse width T3, and frequency spectrum width F1 and period P3. The pulse 672 is frequency offset from the pulse 674, the pulse 676 is frequency offset from the pulse 678, and the pulse 682 is frequency offset from the pulse 684. The pulses 672, 674, 676, 678, 682, and 684 may be applied to an LED module to affect dermatological cells or chemicals 22A and the pins 230, 351, 451. Pulses 672, 674 having different frequency spectrums may enable different LED stimulation. In an embodiment the pulses 672, 676, 682 may be applied to a first LED module and the pulses 674, 678, 684 may be applied to a second LED module. The frequency separation between the respective pulses may enable simultaneous energization of a first and a second LED module and the pins 230, 351, 451 and subsequent and independent spectrum generation.

In an embodiment the invention may employ the algorithm 740 shown in FIG. 7A to apply therapy to dermatological cells. A user, clinician, or equipment may place an apparatus 10, 320, 360, 360, 400, 460 on dermatological cells to be treated (activity 741) including pressing the apparatus against the cells firmly enough to embed one or more pins 251, 351, 451 in the cells. A first signal such as shown in FIGS. 5A, 5B, and 6 may be applied to a first LED module or group (32A) and the pins 230, 351, 451 of a dermatological apparatus 10, 320, 360, 360, 400, 460 (activity 742) for a predetermined time period (activity 744). A second signal such as shown in FIGS. 5A, 5B, and 6 may be applied to a second LED module or group (32B) and the pins 230, 351, 451 of a dermatological apparatus 10, 320, 360, 360, 400, 460 (activity 746) for a predetermined time period (activity 748). The signals applied to the groups may be selected to stimulate dermatological cells or chemicals 22A or cause vibration of one or more pins 251, 351, 451.

In another embodiment the invention may employ the algorithm 750 shown in FIG. 7B to apply therapy to dermatological cells. A user, clinician, or equipment may apply a light sensitive chemical on an apparatus 10, 320, 360, 360, 400, 460 or on dermatological cells to be treated (activity 751). The user, clinician, or equipment may place apparatus 10, 320, 360, 360, 400, 460 on dermatological cells to be treated (activity 752). A signal such as shown in FIGS. 5A, 5B, and 6 may be applied to a LED module or group (32A or 32B) and the pins 230, 351, 451 (activity 354) for a predetermined time period (activity 356).

In another embodiment the invention may employ the algorithm 760 shown in FIG. 7C to apply therapy to dermatological cells. A user, clinician, or equipment may apply a light sensitive chemical on an apparatus 10, 320, 360, 360, 400, 460 or on dermatological cells to be treated (activity 761). The user, clinician, or equipment may place an apparatus 10, 320, 360, 360, 400, 460 on dermatological cells to be treated (activity 762). A first signal such as shown in FIGS. 5A, 5B, and 6 may be applied to a first LED module or group (32A) and one or more pins 251, 351, 451 of a dermatological apparatus 10, 320, 360, 360, 400, 460 (activity 763) for a predetermined time period (activity 764). A second signal such as shown in FIGS. 5A, 5B, and 6 may be applied to a second LED module or group (32B) and one or more pins 251, 351, 451 of a dermatological apparatus 10, 320, 360, 360, 400, 460 (activity 766) for a predetermined time period (activity 768).

The apparatus 10, 320, 360, 360, 400, 460 may be used to employ cosmetic or medications or other chemicals directly on dermatological cells such as skin with the addition of light of specific frequencies for treatment and healing of epidermal cells of the skin or tissue below the skin with the object of assisting the agents used in delivery, uptake, action and function more effectively. The LEDs 32A, 32B may create the specific frequencies of light. The apparatus 10, 320, 360, 360, 400, 460, light application may enable cosmetic or medication or other active chemicals 22A on dermatological cells for longer time periods while preventing dehydration of the applied substances. Such light application may improve the efficacy of cosmetic or medication or other active chemical as a function of the selected wavelengths or frequencies.

Further the dermatological system application may increase cellular activity and help heal tissue faster and facilitate the delivery, uptake and use in the cell of the cosmetics, medications, or chemicals 22A used. The LED light of specific frequencies may increase fibroblast production and collagen as well as other activities of the cell including stimulating the organelles and mitochondria to produce ATP for cell energy for functioning, decreasing treatment time and facilitate healing. The apparatus 10, 320, 360, 360, 400, 460 make the agents used on the body more efficacious and useful to the body on a cellular level.

The apparatus 10, 320, 360, 360, 400, 460 may stimulate the basic energy processes in the mitochondria (energy compartments) of each cell, particularly when near-infrared light is used to activate the color sensitive chemicals (chromophores, cytochrome systems) inside but not limited to these spectrum alone as the UV, other visible and IR spectrums may also be usable. In an embodiment optimal LED wavelengths for skin repair may include 640, 680, 730 nanometers (nm) wavelengths to IR 880 nm. Further application of blue light 400 nm to 490 via the apparatus 10, 320, 360, 360, 400, 460 may inhibit the growth and kill bacteria, fungus in and on dermatological cells. The apparatus 10, 320, 360, 360, 400, 460 may be employed to apply cosmetics, medications and/or other actives directly to the skin and maintain their presence long-term while using LED or other actinic light to increase their effect on the cells and tissue in the body. The apparatus 10, 320, 360, 360, 400, 460 are also highly portability and enable user mobility during treatment.

Chemicals 22A may include cosmetics, medications and other actives appropriate for dermatological cells including AHA's (alpha hydroxy acid), natural oils, aloe vera compounds, collagen boosters, bt, chitosan, daeses, endorphins, photodynamic drugs (PDT) like (Photofrin or ALA), vitamins A, C E or others, kojic acid, retinols or other exfoliant, salicylic acid, anti oxidants or other youth boosters and anti aging cosmetic or medications, antiseptic, antibiotics, anti-cancer agents, aroma therapy agents, fruit and vegetable extracts, anti-inflammatory agents, pain relievers, hormones, depilatories, and others, but the scope of this invention is not limited to these alone but can include any helpful medication, herbal formula or active compound for the skin and/or other tissues.

Figure 8:
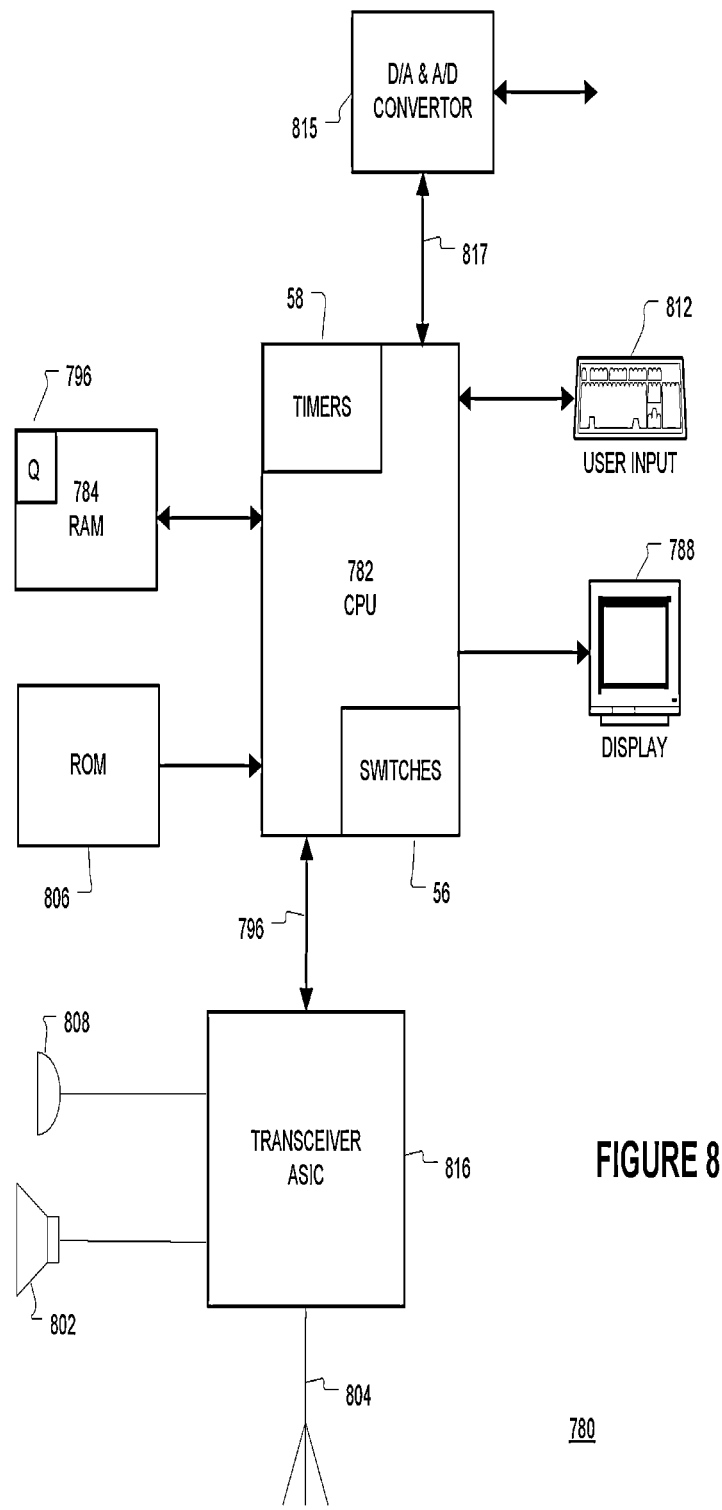
FIG. 8 is a block diagram of an article according to various embodiments.

FIG. 8 is a block diagram of an article 780 according to various embodiments. The article 780 shown in FIG. 8 may be used in various embodiments as a part of apparatus 10, 320, 360, 360, 400, 460 where the article 780 may be any computing device including a personal data assistant, cellular telephone, laptop computer, or desktop computer. The article 780 may include a central processing unit (CPU) 782, a random access memory (RAM) 784, a read only memory (ROM") 806, a display 788, a user input device 812, a transceiver application specific integrated circuit (ASIC) 816, a digital to analog (D/A) and analog to digital (A/D) convertor 815, a microphone 808, a speaker 802, and an antenna 804. The CPU 782 may include an OS module 814 and an application module 813. The RAM 784 may include switches 56 and timers 58.

The ROM 806 is coupled to the CPU 782 and may store the program instructions to be executed by the CPU 782. The RAM 784 is coupled to the CPU 782 and may store temporary program data, overhead information, and the queues 798. The user input device 812 may comprise an input device such as a keypad, touch pad screen, track ball or other similar input device that allows the user to navigate through menus in order to operate the article 780. The display 788 may be an output device such as a CRT, LCD, LED or other lighting apparatus that enables the user to read, view, or hear user detectable signals.

The microphone 808 and speaker 802 may be incorporated into the device 780. The microphone 808 and speaker 802 may also be separated from the device 780. Received data may be transmitted to the CPU 782 via a bus 796 where the data may include signals for an LED 32A, 32B, 332 or optical module or wires 331, 458. The transceiver ASIC 816 may include an instruction set necessary to communicate data, screens, or signals. The ASIC 816 may be coupled to the antenna 804 to communicate wireless messages, pages, and signal information within the signal. When a message is received by the transceiver ASIC 816, its corresponding data may be transferred to the CPU 782 via the serial bus 796. The data can include wireless protocol, overhead information, and data to be processed by the device 780 in accordance with the methods described herein.

The D/A and A/D convertor 815 may be coupled to one or more optical modules to generate a signal to be used to energize one of the optical modules. The D/A and A/D convertor 815 may also be coupled to one devices such as LEDs 32A, 32B and the pins 251, 351, 451. Any of the components previously described can be implemented in a number of ways, including embodiments in software. Any of the components previously described can be implemented in a number of ways, including embodiments in software. Thus, the LEDs 32A, 32B, pins 251, 351, 451, controllers 54, switch 56, timers 58, controller 320 may all be characterized as "modules" herein. The modules may include hardware circuitry, single or multi-processor circuits, memory circuits, software program modules and objects, firmware, and combinations thereof, as desired by the architect of the system 10, 30, 50, 60 and as appropriate for particular implementations of various embodiments.

Figure 9B:
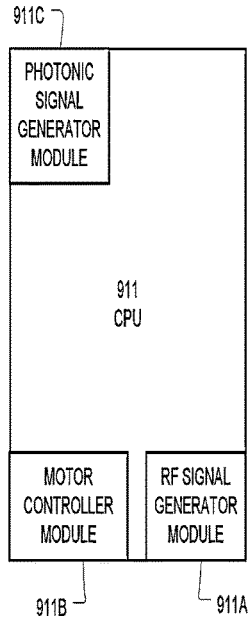
FIG. 9B is a block diagram of an article according to various embodiments that may be employed in architecture of FIG. 9A.
Figure 9A:
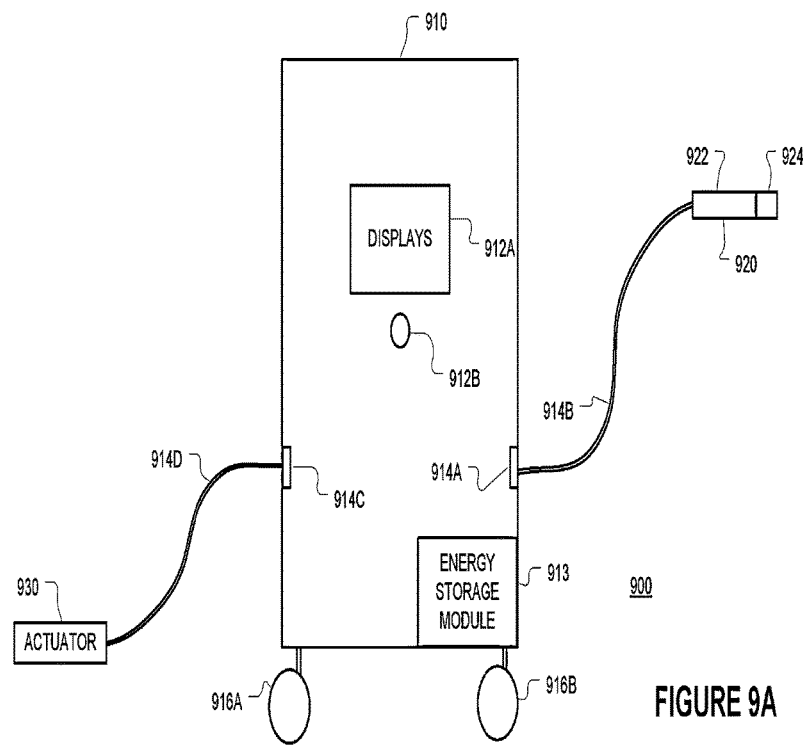
FIG. 9A is a simplified block diagram of a dermatological treatment architecture according to various embodiments.

FIG. 9A is a simplified block diagram of a dermatological treatment architecture (DTA) 900 according to various embodiments. As shown in FIG. 9A, architecture 900 includes a signal generation and control module (SGC) 910, a handle module 920, and an actuator module 930. In an embodiment the handle module 920 may include a deployable needle module 924 and a motor and LED module 922. In an embodiment the deployable needle module 924 may be releasably coupled to the motor and LED module 922. In a further embodiment the deployable needle module 924 may be a disposable cartridge module 924 to be removed and disposed after one or more treatments or for each patient, client, or user.

The SGC 910 may include one or more displays 912A, user input device 912B, handle module interface 914A, and actuator module interface 914C, electrical energy storage module 913, and one or more wheels 916A, 916B. In an embodiment the SGC 910 may be moveable and the wheels 916A, 916B may be lockable to prevent unintentional movement of the SGC 910 once positioned where desired by a user. In another embodiment the SGC 910 may also be coupled to the external power source including an alternating current (AC) grid source.

In an embodiment the displays 912A may indicate operational parameters for a hand module 920 to be coupled or coupled to the SGC 910. The displays 920 may be touch sensitive so a user may configure one or more operational parameters. In an embodiment the operational parameters may include electrical energy signal intensity to be applied the hand module 920, timing of such energy application, needle deployment timing and depth(s), LED intensity and timing, and number of cycles or shots to be conducted for each actuation via the actuator 930. In an embodiment the actuator 930 may be integral to the SGC 910 or a separate device wireless coupled or wired to the SGC 910 via a cable 914D and the SGC 910 actuator module interface 914C.

In an embodiment the actuator 930 may a mechanical device including a foot actuator or hand based actuator. The actuator 930 may also be an electronic device having an ASIC or running an application on a device (such as a computer, laptop, PDA, cellphone, or other electronic device) such as the module 780 shown in FIG. 8. In an embodiment the application may enable a user to set or control any of the possible operational parameters of the SGC 910 and initiate actuation a device 920 coupled to the SGC 910. FIG. 9B is a block diagram of a CPU module 911 that may be employed in the SGC 910 according to various embodiments.

The CPU module 911 may include a radio frequency (RF) signal generator (RFSG) module 911A, a needle deployment motor controller (NDMC) module 911B, and a photonic signal generator module (PSG) 911C. In an embodiment the photonic signal generator module 911C may be an LED signal generator or controller module 911C. In an embodiment a hand module 920 may include one or more photonic generation devices or modules (922I in FIG. 10A, 10B) where the PSG 911C may generate control or energy signals that cause the photonic modules 922I to generate photons of one or more frequencies with a desired intensity.

The NDMC 911B may control the deployment of one or more needles 924A of a deployable needle module 924 (FIG. 9C) based on one or more user selected operational parameters. The parameters may determine the depth and duty cycle related to the needle(s) 924A deployment in an embodiment. The signals generated by the NDMC 911B to control needle deployment may vary as a function of motor (s) (922A, FIG. 9C) employed to drive one or more needles 924A. As described above an electrical signal may also be applied to the needle(s) 924A to cause vibration of the needles or enable cutting, blending, and coagulation of the tissue in which the needles 924A are deployed. The RFSG 911A may generate one or more electrical signals to be applied to one or more needles 924A based on the selected operational parameters. An electrical signal may be applied to a single needle 924A, group of needles 924A (mono-polar configuration) or pair(s) of needles 924A (bipolar configuration) in an embodiment. In an embodiment the RFSG 911A may apply signals 650, 630, 640, 670 shown in FIGS. 5A, 5B, and 6, a combination thereof, or other signals.

In an embodiment the CPU module 911 via the RFSG 911A, NDMC 911B, and PSG 911C may create various therapy solutions including various combinations of photonic, electrical, and mechanical (needle deployment) therapy. In a further embodiment the CPU module 911 may control the generation of photonic energy to particular modules 922I, individual or group of needle(s) 924A deployment via one or more motors 922A, and control electrical signal(s) applied to individual or group of needles 924A. Accordingly the DTA 900 may apply various therapies based on user selections via the displays 912A, user selection device 912B, and actuator 930. The CPU 911 may employ the algorithm 930 (FIG. 12) or variations thereof to control the operation of the DTA 900.

Figure 9C:
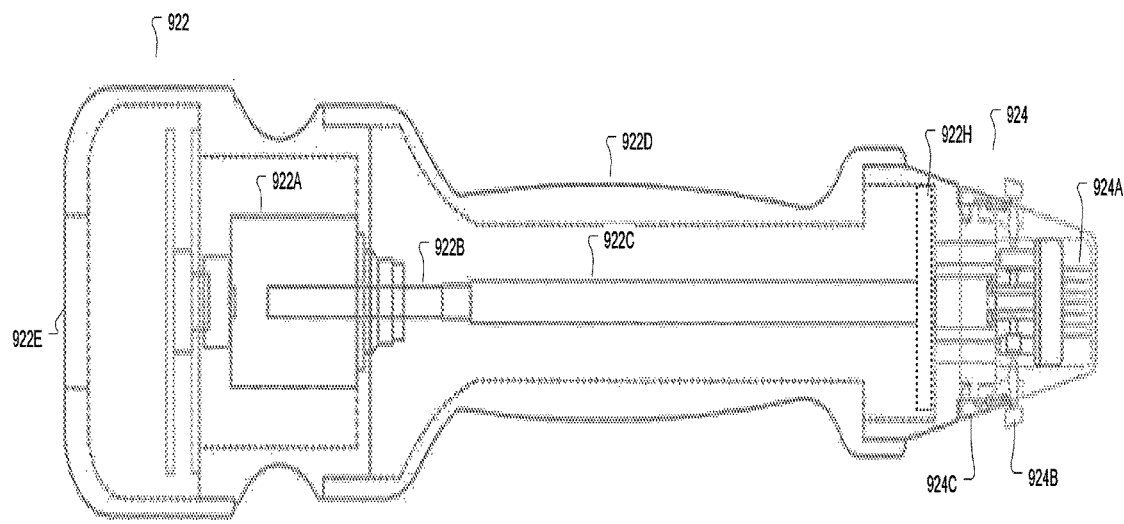
FIG. 9C is a simplified cross-sectional diagram of a cartridge based dermatological treatment apparatus with the needles retracted according to various embodiments.
Figure 9D:
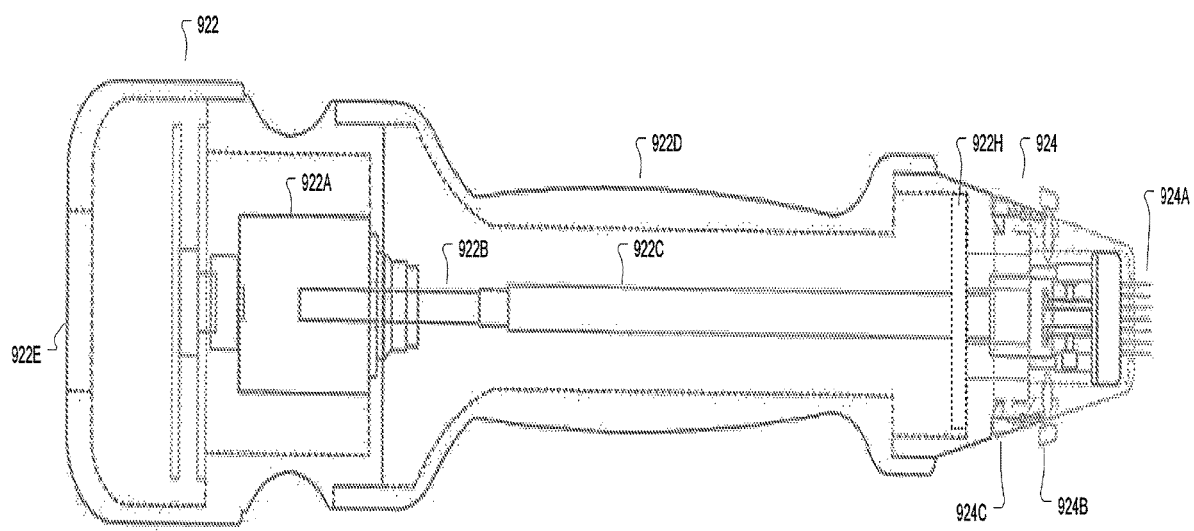
FIG. 9D is a simplified cross-sectional diagram of a cartridge based dermatological treatment apparatus with the needles deployed according to various embodiments.

FIG. 9C is a simplified cross-sectional diagram of a cartridge based dermatological treatment apparatus or hand module 920 with one or more needles 924A retracted according to various embodiments. FIG. 9D is a simplified cross-sectional diagram of a cartridge based dermatological treatment apparatus or hand module 920 with one or more needles 924A deployed according to various embodiments. The handle module 920 may include a deployable needle module (DNM) 924 and a motor and LED module (MLM) 922. In an embodiment the DLM 924 may be a releasably couplable cartridge module. In a further embodiment the DLM 924 may be a detachable cartridge module (DCM) 924 where the DCM may be changed between therapy application(s) or client(s). In a further embodiment, the DCM 924 may be disposed after usage or cleaned via an autoclave or chemical process.

As shown in FIGS. 9C and 9D, the MLM 922 may include one or more motors 922A, longitudinally extendable drive arms 922B, drive shaft 922C, outer casing 922D, signal interface 922F, photonic generator module 922H, and DCM 924 interface 925 (shown in FIGS. 10A to 10F). The motor(s) 922A and photonic generator module 922H may be electrically coupled to the signal interface 922E to received control signals and energy to operate one or more motors 922A and photonic devices or modules 922I of the photonic generator module 922H. The drive arm(s) 922B may be coupled to one or more drive shafts 922C so the drive shafts may be moved longitudinally to deploy and retract one or more needles 924A when the MLM 922 is operatively coupled to the DNM 924.

Figure 10A:
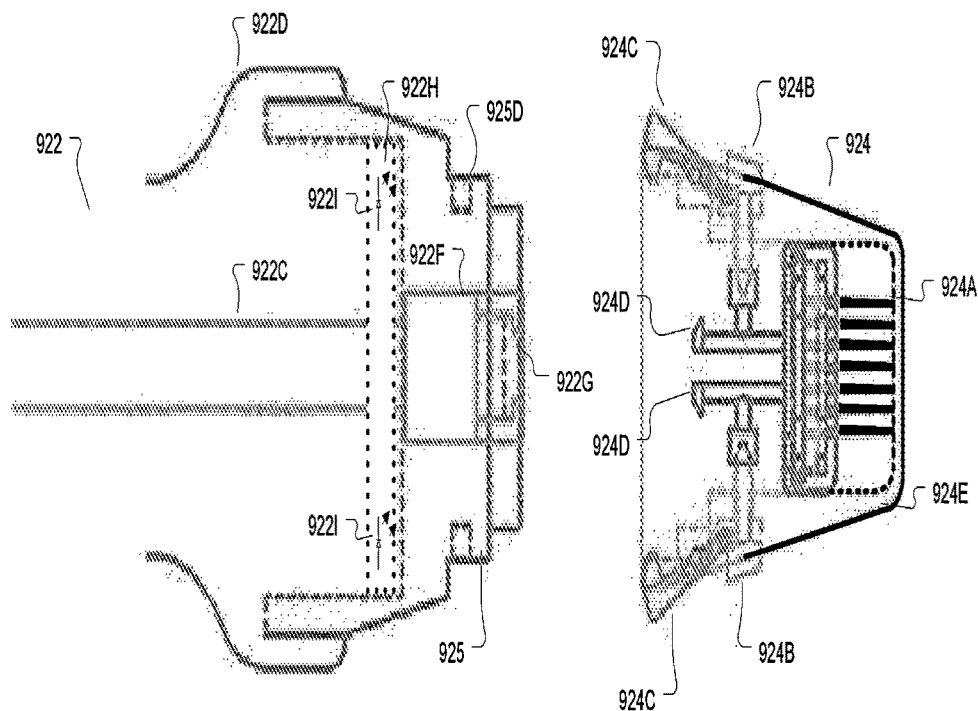
FIG. 10A-10D are simplified, partial, cross-sectional diagrams of a cartridge in various stages of attachment to a dermatological treatment apparatus according to various embodiments.
Figure 10B:
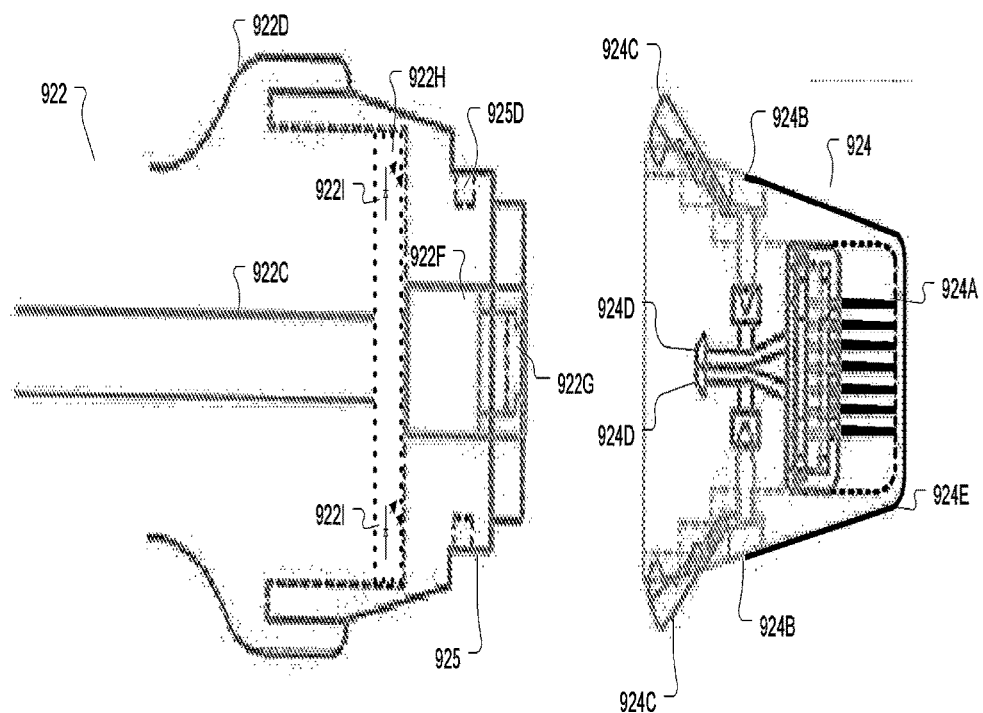
Figure 10C:
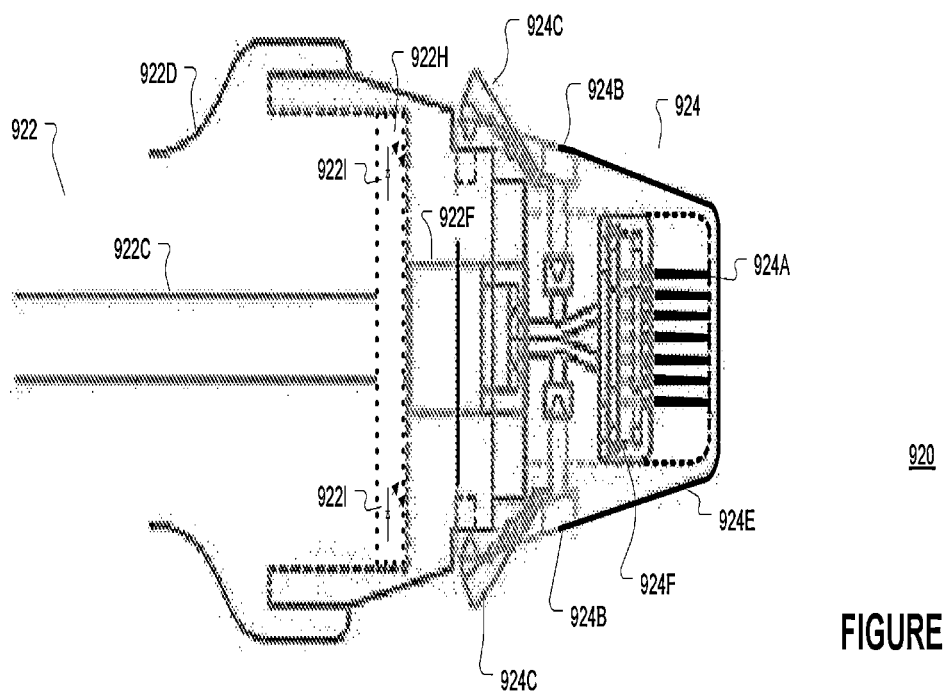

As shown in FIGS. 9C and 9D the deployable needle module 924 may include at least one deployable needle 924A, MLM connecting arm and drive coupling tabs 924B, and MLM connecting/locking arms 924C. The MLM connecting/locking arms 924C may be configured to engage and lock to DCM 924 interface 925 recesses 925D (FIG. 10F). The MLM connecting arm and drive coupling tabs 924B may be configured to disengage connecting/locking arms 924C from the MLM interface 925 when the tabs 924B are depressed inward in an embodiment (as shown in FIG. 10B). The tabs 924B may further displace drive shaft connecting arms 924D (FIG. 10A) inward or centrally when the tabs 924B are depressed inwardly (as also shown in FIG. 10B). When the connecting/locking arms 924C are depressed inwardly or centrally (FIGS. 9C and 9D) from an outward position (FIG. 10B). The arms 924C may engage the interface 925 recesses 925D to securely hold the DNM 924 to the MLM 922. The arms 924C may also displace the tabs 924B outwardly and cause the drive shaft connecting arms 924D to return outwardly.

Figure 10D:
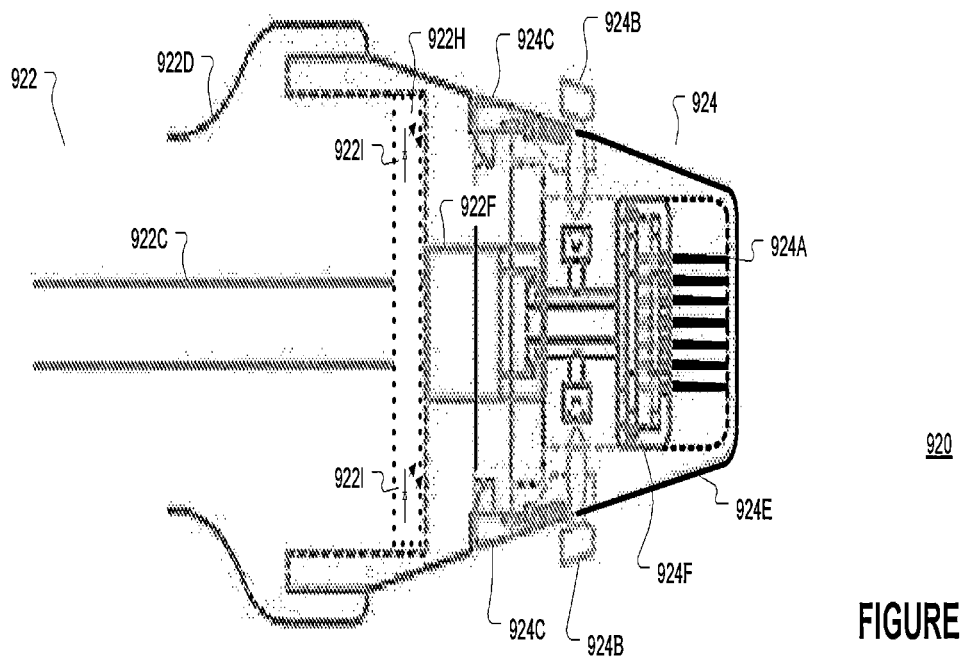
Figure 10E:
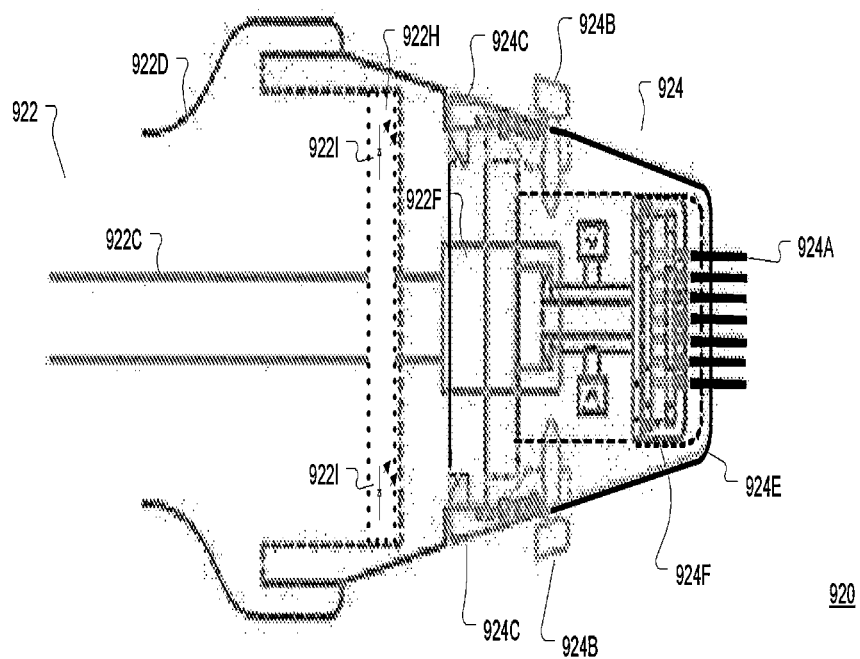
FIG. 10E is a simplified, partial, cross-sectional diagram of a dermatological treatment apparatus with needles deployed according to various embodiments.
Figure 10F:
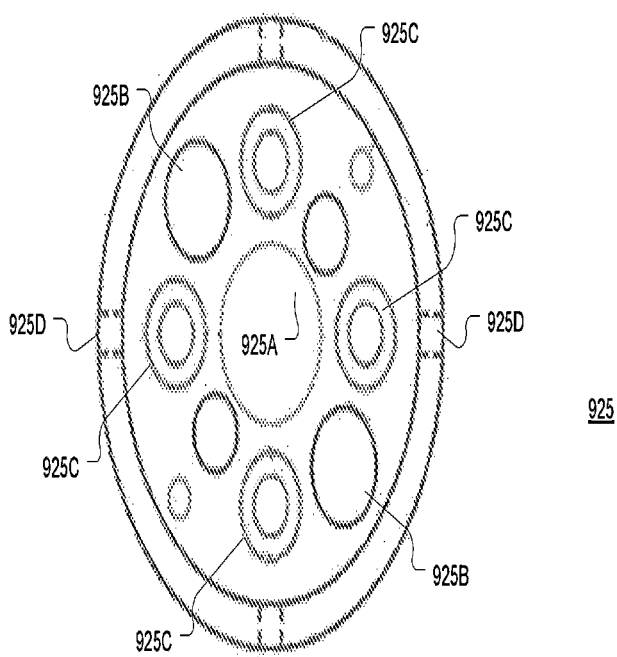
FIG. 10F is a simplified cross-sectional diagram of a cartridge based dermatological treatment apparatus cartridge interface according to various embodiments.

The drive shaft connecting arms 924D may securely engage the drive shaft 922C tip 922F (FIG. 10E) recess 922G (FIG. 10E) when they return to an outward position as shown in FIGS. 10D and 10E. In this configuration the DNM 924 is securely coupled to the MLM 922 via the arms 924C and 924D. In this configuration the motor(s) 922A via drive shaft(s) 922C coupled to the motor 922A shaft 922B may reliably drive one or more needles 924A of the DNM 924 (from a retracted or deployed position such as shown in FIGS. 9C and 9D, respectively). Further the motor(s) 922A may include steps or infinite drive extension 922B control to enable precise needle deployment depth or extension beyond the DNM 924 shell (924E, FIG. 10A).

FIG. 10A-10D are simplified, partial, cross-sectional diagrams of the DNM 924 in various stages of attachment to the MIM 922 via the arms 924C and 924D according to various embodiments. As shown in FIG. 10A the DNM or DCM 924 is decoupled from the MLM 922. The MLM 922 includes the photonic generator module (PGM) 922H, interface 925, and drive shaft tip 922F in a distal portion. As shown in FIG. 10A the PGM 922H may include one or more photon modules 922I. The photon modules 922I may be LED modules and emit photon with various frequencies and intensities based on the PSG 911C control signal.

As shown in FIG. 10A the DNM or DCM 924 may include the connecting arms 924C, deflecting tabs 924B, drive shaft coupling arms 924D, outer shell 924E, and one or more needles 924A. In an embodiment the drive shaft coupling arms 924D may include tabs that may securely engage the drive shaft tip 922F recess 922G. The drive shaft coupling arms 924D may be returnably deflectable inwardly (as shown in FIG. 10B) via inward depression of the tabs 924B. Such inward depression of the tabs 924B may deflect the coupling arms 924C outward. Similarly, inward depression of the coupling arms 924C to engage the interface 925 recesses 925D securely may deflect the tab arms 924B outwardly (relative the central axis of the DNM 920). Such outward movement may enable the drive shaft coupling arms 924D to return to a non-deflected state as shown in FIG. 10A.

In an embodiment a DNM or DCM 924 may be securely coupled to a MLM 922 by first completely compressing the arms or tabs 924B as shown in FIG. 10B. As noted above such inward compression may cause the coupling arms 924C to deflect outwardly and the drive shaft coupling arms 924D to be deflected inwardly towards each other. The drive shaft coupling arms 924D may be compressed so they may fit within the drive shaft 922C tip 922F recess 922G as the DNM or DCM 924 is advanced toward the MLM 922 distal end to securely couple the DNM 924 to the MLM 922 (as shown in FIG. 10D). After the DNM or DCM 924 is placed over the MLM 922 distal end so the drive shaft coupling arms 924D are located within the drive shaft 922C tip 922F recess 922G and the coupling arms 924C are adjacent the MLM 922 interface 925 recesses 925D as shown in FIG. 10C.

To complete the coupling of a DNM 924 to the MLM 922, the coupling arms 924C may compressed inwardly as shown in FIG. 10D. The compression of the coupling arms 924C may deflect the tabs or arms 924B outwardly. Such outward deflection of the arms 924B may enable the drive shaft coupling arms 924D to return to a non-deflected state and securely engage the MLM 922 drive shaft 922C tip 922F recess 922G (as shown in FIG. 10D). In an embodiment a single coupling arm 924C, drive shaft coupling arm 924D, and tab 924B may be employed in an DNM 924. After the secure coupling of the DNM 924 to the MLM 922, the MLM 922 via the motor(s) 922A may controllably deploy one or more needles 924A as shown in FIG. 10E. FIG. 10F is a simplified cross-sectional diagram of a DNM interface 925 according to various embodiments.

As noted the interface 925 may include one or more recesses 925D to be securely engaged to DNM 924 coupling arms 924C. The interface 925 may also include several fenestrations or openings 925A, 925B, 925C (FIG. 10F). The central fenestration 925A may be sized to enable passage of the MLM 922 drive shaft 922C tip 922F. The fenestrations 925C may be sized and located above one or more photon modules 922I to enable photons generated by the photon modules 922I to pass into the DNM 924. In an embodiment the DNM 924 outer casing 924E may be translucent and act as a waveguide to communicate photons to the needle area of the DNM 924. The fenestrations 925B may be sized and configured to enable electrical coupling pins 924G (FIG. 11A) passage from the DNM 924 to electrical couplings of the MLM 922. The pins 924G may communicate electrical signals from the RFSG 911A to one or more needles 924A via the wires 914B and MLM 922.

Figure 11A:
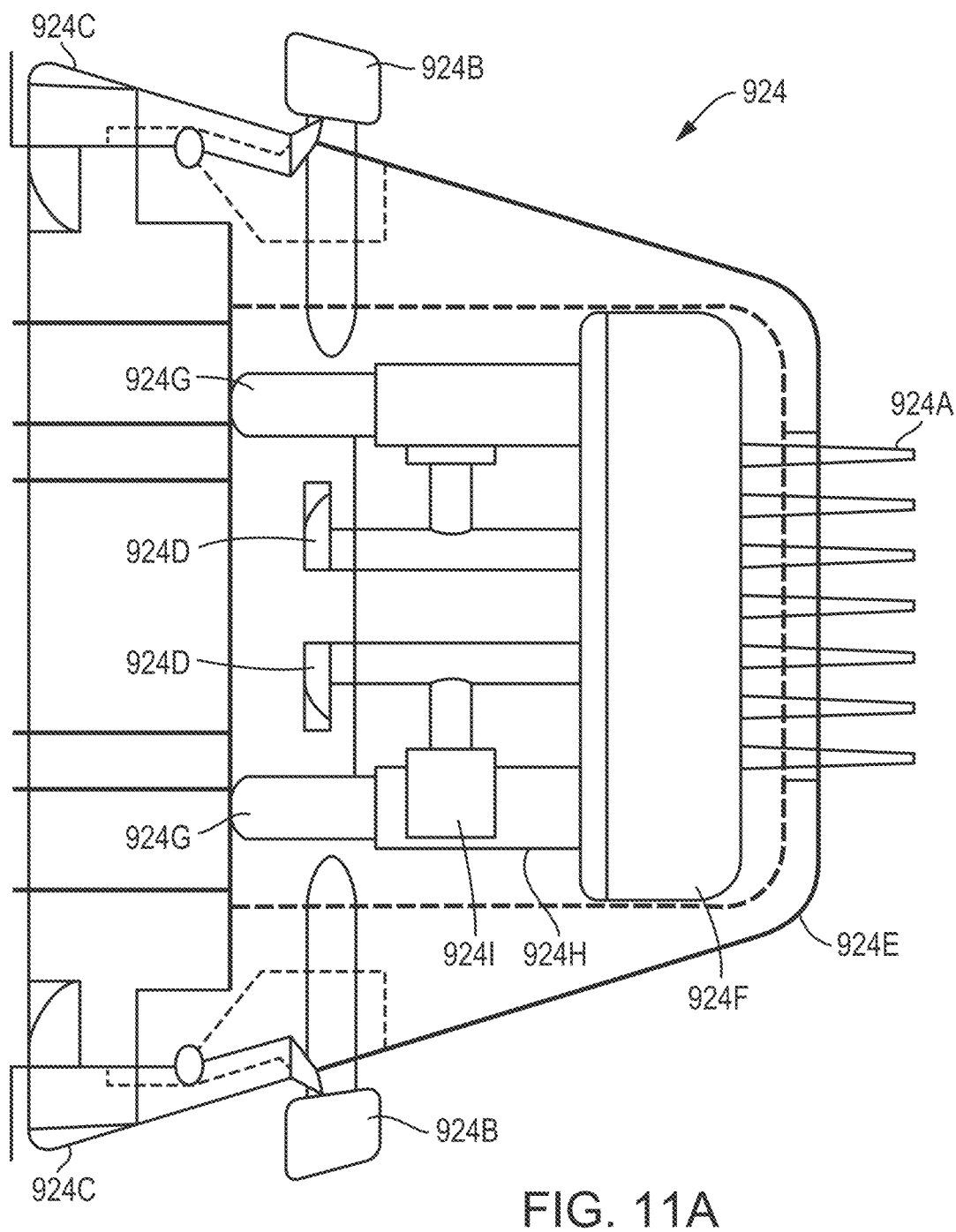
FIG. 11A is a simplified, partial, cross-sectional diagram of a dermatological treatment apparatus cartridge coupled to a handle with needles deployed according to various embodiments.

FIG. 11A is a simplified, partial, cross-sectional diagram of DNM 924 coupled to a MLM 922 with needles 924A deployed according to various embodiments. As shown in FIG. 11A, the DNM 924 may further include electrical coupling pins 924G set with a spring loaded base 924H (in an embodiment). As noted the pins 924G may extend to electrical contacts in the MLM 922 via the interface 925 fenestrations 925B. Although a pair of pins 924G is shown, one or more pins 924G may be employed in a DNM 924 according to various embodiments. A drive shaft coupling arm 924D may include an offset 924I where the offset may be configured to engage a tab or arm 924B.

Figure 11B:
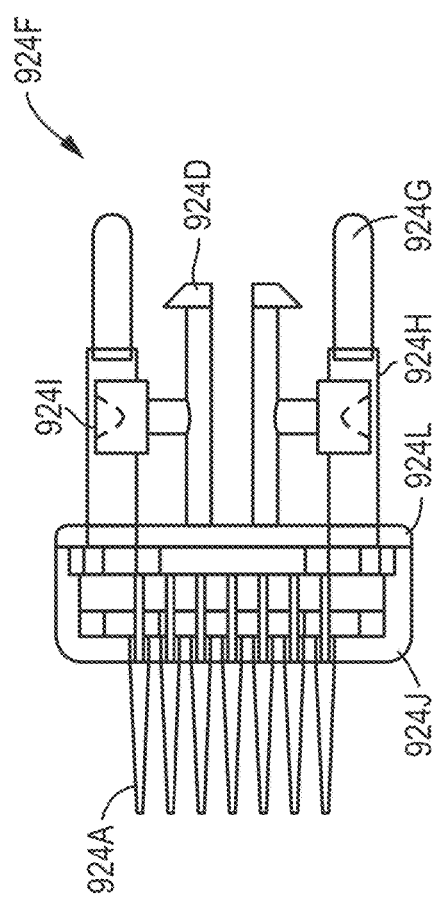
FIG. 11B is a simplified, cross-sectional diagram of a cartridge needle assembly according to various embodiments.
Figure 11C:
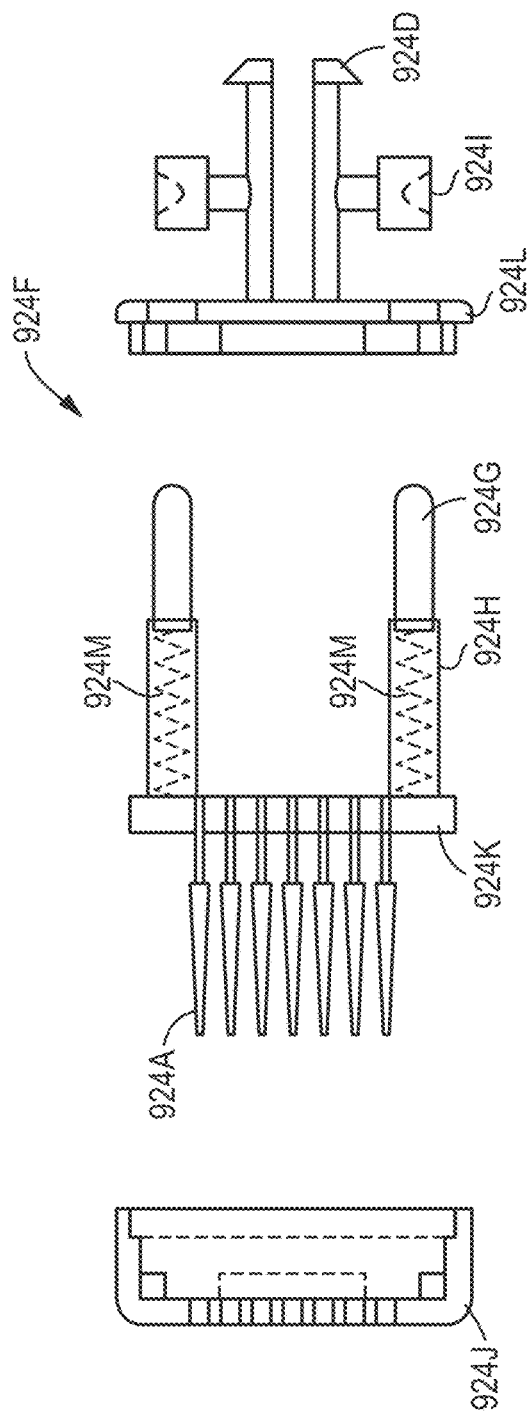
FIG. 11C is a simplified, cross-sectional, exploded diagram of a cartridge needle assembly according to various embodiments.

As shown in FIG. 11A when the needle array or assemble 924F is deployed depression of the tabs 924B inwardly will not engage the drive shaft coupling arms 924D (via the offsets 924I). Such a configuration may prevent unintentional decoupling of the DNM 924 to the MLM 922 when the needle assembly 924F is at least partially deployed. As shown in FIG. 11A, the electrical contact pin 924G is sized to fit within the spring loaded based 924H. In an embodiment the internal spring 924M (FIG. 11C) may force extension of the pin 924G to maintain electrical conduction with the MLM 922 as the needle assembly 924F is moved (recessed and deployed to various depths). FIG. 11B is a simplified, cross-sectional diagram of a DNM 924 needle assembly 924F according to various embodiments. FIG. 11C is a simplified, cross-sectional, exploded diagram of the DNM 924 needle assembly 924F according to various embodiments. As shown in FIGS. 11B and 11C, the needle assembly 924F may include a pin cover 924J, drive arm module 924L, needles 924A, pins 924G with bases 924H, and needle printed circuit board (PCB) 924K.

In an embodiment the PCB 924K may couple one or more needles 924A to a first pin 924G base 924H and another one or more needles 924A to another pin 924G based 924H. The first pin 924G and second pin 924H may couple alternating rows or columns of needles 924A to form one or more dipoles between such needles 924A. The drive shaft coupling arms 924D may have a base 924L where the cover 924J includes fenestrations for the needles 924A, a recess for the PCB 924K, and an outer recess for the coupling arm base 924L (as shown assembled in FIG. 11B).

Figure 12:
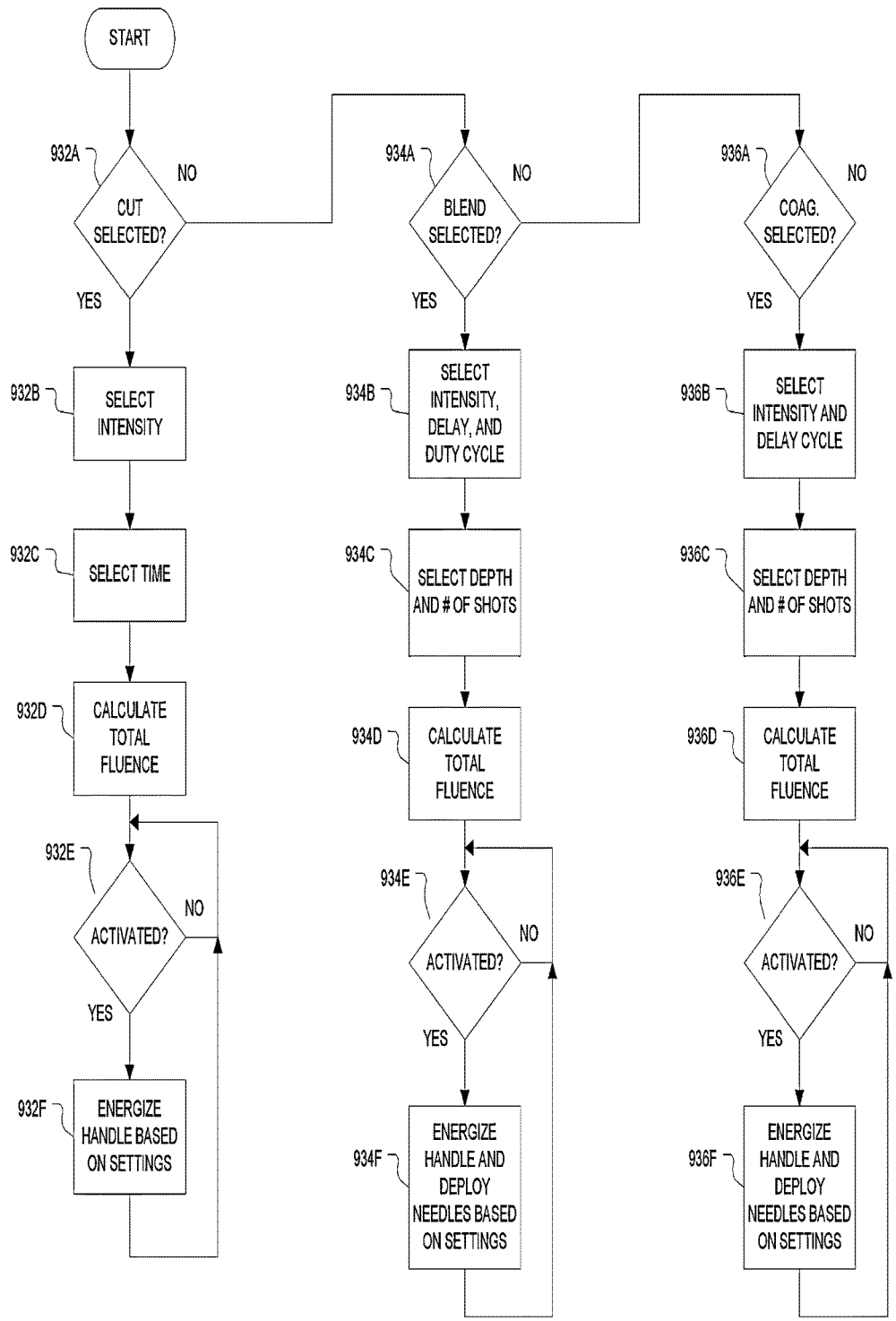
FIG. 12 is a flow diagram illustrating a dermatological treatment system processing algorithms according to various embodiments.

FIG. 12 is a flow diagram illustrating a DTA 900 processing algorithms 930 according to various embodiments. As noted the DTA 900 SGC 911 RFSG 911A, NDMC 911B, and PSG 911C may enable a user or clinician to select a variety of operational parameters to deliver a desired combination of electrical, light (photonic), and mechanical (needle) therapy to dermatological tissue. In the algorithm 930, a user may select different operational modes including cut (activities 932A to 932F), blend (activities 934A to 934F), and coagulation (activities 936A to 936F) in an embodiment. In a cut operational mode, a user may select the electrical signal intensity (activity 932B) and application time (activity 932C). The CPU 911 may determine the total energy that will be applied for each activation based on the selected intensity and time (total fluence—activity 932D). Then, upon activation (activity 932E, 932F) the DTA 900 may energize the MLM 922 based on the operational parameters.

In a blend operational mode (activity 934A), a user may select the electrical signal intensity, start delay, and duty cycle (activity 934B) and needle deployment depth and number of shots per activation (activity 934C). The duty cycle may include the delay before energy and needle deployment, the time the energy and needles are deployed, and the subsequent off or rest time before the next possible duty cycle. As noted above the motor(s) 922A may enable precise needle extension (effective depth) control. In an embodiment the motor(s) 922A may include a transverse motor that converts rotational force to longitudinal force. The motor may be a Haydon model number: 21H4AB-05-049 having a motor speed of about 0.005 mm/msec and motor power of about 1000 Hz approximately 40N (Newton) (described in detail at www.haydonkerk.com and whose specifications are incorporated by reference).

The CPU 911 may determine the total energy that will be applied for each activation based on the selected intensity and duty cycle (total fluence—activity 934D). Then, upon activation (activity 934E, 934F) the DTA 900 may energize the MLM 922 based on the operational parameters and deploy the needle assembly 924F to a desired extension beyond the DNM 924 shell 924E to enable a desired depth of needle 924A penetration within tissue when the shell 924E is placed adjacent the tissue.

In a coagulation operational mode (activity 936A), a user may select the electrical signal intensity and start delay (activity 936B) and needle deployment depth and number of shots per activation (activity 936C). As noted above the motor(s) 922A may enable precise needle extension (effective depth) control. The CPU 911 may determine the total energy that will be applied for each activation based on the selected intensity (total fluence—activity 936D). Then, upon activation (activity 936E, 936F) the DTA 900 may energize the MLM 922 based on the operational parameters and deploy the needle assembly 924F to a desired extension beyond the DNM 924 shell 924E to enable a desired depth of needle 924A penetration within tissue when the shell 924E is placed adjacent the tissue.

Applications that may include the novel apparatus and systems of various embodiments include electronic circuitry used in high-speed computers, communication and signal processing circuitry, modems, single or multi-processor modules, single or multiple embedded processors, data switches, and application-specific modules, including multilayer, multi-chip modules. Such apparatus and systems may further be included as sub-components within a variety of electronic systems, such as televisions, cellular telephones, personal computers (e.g., laptop computers, desktop computers, handheld computers, tablet computers, etc.), workstations, radios, video players, audio players (e.g., mp3 players), vehicles, medical devices (e.g., heart monitor, blood pressure monitor, etc.) and others. Some embodiments may include a number of methods.

It may be possible to execute the activities described herein in an order other than the order described. Various activities described with respect to the methods identified herein can be executed in repetitive, serial, or parallel fashion.

A software program may be launched from a computer-readable medium in a computer-based system to execute functions defined in the software program. Various programming languages may be employed to create software programs designed to implement and perform the methods disclosed herein. The programs may be structured in an object-orientated format using an object-oriented language such as Java or C++. Alternatively, the programs may be structured in a procedure-orientated format using a procedural language, such as assembly or C. The software components may communicate using a number of mechanisms well known to those skilled in the art, such as application program interfaces or inter-process communication techniques, including remote procedure calls. The teachings of various embodiments are not limited to any particular programming language or environment.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. § 1.72 (b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. An apparatus for treating dermatological tissue, comprising:
   a user holdable device, an end of the user holdable device defining a surface configured to receive a needle module,
      wherein the end of the user holdable device is capable of being releasably coupled to the needle module that includes a movable needle assembly that includes a plurality of needles, wherein the needle assembly is located past the end of the user holdable device when the needle module is releasably coupled to the user holdable device, and
      wherein the user holdable device includes a motor capable of moving the needle assembly to deploy the plurality of needles to penetrate dermatological tissue to a desired depth, and wherein the desired depth is selectable by a user;
   a signal generator, wherein the signal generator is capable of being coupled to the plurality of needles to provide a radio frequency signal, and wherein an intensity of a radio frequency signal is selectable by the user;
   at least one processor,
      wherein the at least one processor is configured to provide a signal to cause the motor to deploy the plurality of needles to the desired depth,
      wherein the at least one processor is configured to provide a signal to cause the signal generator to provide the intensity of the radio frequency signal to the plurality of needles; and
   at least one display.

2. The apparatus for treating dermatological tissue of claim 1, wherein the at least one display is a touch sensitive display, wherein the touch sensitive display displays options to a user to select a plurality of operational parameters, wherein the desired depth is one of the plurality of operational parameters, and wherein an intensity of a radio frequency signal is one of the plurality of operational parameters.

3. The apparatus for treating dermatological tissue of claim 2, wherein at least one of a timing of application of the signal or a timing of needle deployment is one of the plurality of operational parameters.

4. The apparatus for treating dermatological tissue of claim 3, wherein at least one of a number of cycles or number of shots of application of the signal is one of the plurality of operational parameters.

5. The apparatus for treating dermatological tissue of claim 1, wherein the processor is configured to determine an applied total energy based on the selected intensity.

6. The apparatus for treating dermatological tissue of claim 1, further comprising an actuator on a foot pedal, and wherein actuation of the actuator causes needle deployment.

7. The apparatus for treating dermatological tissue of claim 1, further comprising spring pins, wherein the spring pins are electrically coupled to the plurality of needles, and wherein the spring pins extend and compress along the same axis as the plurality of needles.

8. The apparatus for treating dermatological tissue of claim 7, wherein the needle assembly includes a translucent section, and wherein the user holdable device includes at least one LED, and wherein energizing the at least one LED illuminates the plurality of needles via the needle assembly translucent section.

9. A handle of an apparatus for treating dermatological tissue, comprising:
   a user holdable device, an end of the user holdable device defining a surface configured to receive a needle module;
   a needle module that is releasably couplable from an end of the user holdable device, wherein the needle module includes a movable needle assembly that includes a plurality of needles, and wherein the movable needle assembly is located past the end of the user holdable device when the needle module is releasably coupled to the user holdable device;
   a motor capable of moving the needle assembly to deploy the plurality of needles to penetrate dermatological tissue to a desired depth, wherein the desired depth is selectable by a user; and
   spring pins, wherein the spring pins are electrically coupled to the plurality of needles, and wherein the spring pins extend and compress along the same axis as the plurality of needles.

10. The handle of an apparatus for treating dermatological tissue of claim 9, wherein the needle assembly includes a translucent section, and wherein the user holdable device includes at least one LED, and wherein energizing the at least one LED illuminates the plurality of needles via the needle assembly translucent section.

11. The handle of an apparatus for treating dermatological tissue of claim 9, in which the motor is configured to receive a signal to move the needle assembly to deploy the plurality of needles to penetrate dermatological tissue to the desired depth, wherein the desired depth can vary based on the signal received by the motor.

12. A method of treating dermatological tissue, comprising:
- releasably coupling a needle module to a user holdable device, an end of the user holdable device defining a surface configured to receive the needle module;
- placing an end surface of the needle module on or near dermatological tissue to be treated,
  - wherein the needle module includes a needle assembly with a plurality of needles, the needle assembly is located past the end of the user holdable device when the needle module is releasably coupled to the user holdable device, and the needle assembly is movable within the needle module to extend the plurality of needles a desired depth into dermatological tissue, and
  - wherein the needle module is releasably couplable from a user holdable device;
- selecting operational parameters, including the desired depth, an intensity of a radio frequency signal to be provided to the plurality of needles, and a time interval for application of the radio frequency signal;
- communicating a signal to a motor on the user holdable device to extend the plurality of needles to the desired depth; and
- communicating radio frequency signals to the plurality of needles at the intensity and for the time interval selected.

13. The method of treating dermatological tissue of claim 12, in which the operational parameters are selected using a touch sensitive display.

14. The method of treating dermatological tissue of claim 13, in which the operational parameters further comprise at least one of a time interval for needle deployment, a number of cycles, or a number of shots of application of the signal.

15. The method of treating dermatological tissue of claim 12, in which the intensity of the radio frequency signal determines a total energy applied via the plurality of needles.

16. The method of treating dermatological tissue of claim 12, further comprising actuating an actuator on a foot pedal to cause deployment of the needles.

17. The method of treating dermatological tissue of claim 12, the method further comprising extending and compressing spring pins along the same axis as the plurality of needles.

18. The method of treating dermatological tissue of claim 17, wherein the needle assembly includes a translucent section and wherein the user holdable device includes at least one LED, and the method further comprises energizing the at least one LED to illuminate the plurality of needles via the needle assembly translucent section.

* * * * *